US006824740B1

(12) United States Patent
Sheldon, III et al.

(10) Patent No.: US 6,824,740 B1
(45) Date of Patent: Nov. 30, 2004

(54) APPARATUS FOR ACTIVE BIOLOGICAL SAMPLE PREPARATION

(75) Inventors: Edward L. Sheldon, III, San Diego, CA (US); Thomas R. Jackson, La Jolla, CA (US); Paul D. Swanson, Santee, CA (US); Bradley S. Scott, San Diego, CA (US); Michael J. Heller, Encinitas, CA (US)

(73) Assignee: Nanogen, Inc., San Diego, CA (US)

( * ) Notice: Subject to any disclaimer, the term of this patent is extended or adjusted under 35 U.S.C. 154(b) by 0 days.

(21) Appl. No.: 09/561,318

(22) Filed: Apr. 28, 2000

Related U.S. Application Data

(62) Division of application No. 08/709,358, filed on Sep. 6, 1996, now Pat. No. 6,129,828.

(51) Int. Cl.[7] ............................ B01L 11/00; C12M 1/00; C12Q 1/00; C12Q 1/68
(52) U.S. Cl. ................... 422/99; 422/100; 204/518; 204/542; 204/543; 204/544; 204/627; 435/287.2; 435/288.5
(58) Field of Search ................... 204/518, 542, 204/543, 544, 627, 641, 604, 607, 608; 435/287.2, 288.2, 287.3, 288.3, 288.4, 288.5, 288.6, 288.7; 422/99, 100

(56) References Cited

U.S. PATENT DOCUMENTS 3,346,479 A    10/1967    Natelson ................ 204/615

(List continued on next page.)

FOREIGN PATENT DOCUMENTS

DE         2 051 715        4/1972

(List continued on next page.)

OTHER PUBLICATIONS

Camag, Inc. Product Literature.

(List continued on next page.)

Primary Examiner—Nam Nguyen
Assistant Examiner—John S. Starsiak, Jr.
(74) Attorney, Agent, or Firm—O'Melveny & Myers LLP

(57) ABSTRACT

Systems and methods for the electronic sample preparation of biological materials utilize the differential charge-to-mass ratio and/or the differential affinity of sample constituents to separation materials for sample preparation. An integrated system is provided for performing some or all of the processes of: receipt of biological materials, cell selection, sample purification, sample concentration, buffer exchange, complexity reduction and/or diagnosis and analysis. In one embodiment, one or more sample chambers adapted to receive a buffer solution are formed adjacent to a spacer region which may include a trap or other affinity material, electrophoretic motion of the materials to be prepared being effected through operation of electrodes. In another aspect of this invention, a transporter or dipstick serves to collect and permit transport of materials, such as nucleic acids, most preferably DNA and/or RNA. In one embodiment, a membrane or trap is held in a frame which is adapted to mate with a channel formed in the spacer region. In another aspect of this invention, an electrophoretic system for biological sample preparation is operated in a manner so as to utilize the differential charge-to-mass ratio so as to control the migration of materials within the solution. In one aspect, bunching of selected materials is achieved by operation of two electrodes in a manner so as to reduce the spatial dispersion of those materials. In another aspect of this invention, a vertically disposed sample preparation unit includes an upper reservoir including and a collection chamber. A sample is preferably pre-prepared and densified, applied to the conductive polymer, electrophoresed so as to move nucleic acids into the conductive polymer and move undesired material away from the conductive polymer. Integrated systems are described in which cell separation, purification, complexity reduction and diagnosis may be performed together. In the preferred embodiment, cell separation and sample purification are performed in a first region, the steps of denaturation, complexity reduction and diagnosis being performed in a second region.

6 Claims, 14 Drawing Sheets

U.S. PATENT DOCUMENTS

| | | | |
|---|---|---|---|
| 3,375,187 A | 3/1968 | Buchler | 204/613 |
| 3,533,933 A | 10/1970 | Strauch | 204/461 |
| 3,539,493 A | 11/1970 | Dorman | 204/615 |
| 3,616,454 A | 10/1971 | Levy et al. | 204/615 |
| 3,627,137 A | 12/1971 | Bier | 210/321.75 |
| 3,640,813 A | 2/1972 | Nerenberg | 204/615 |
| 3,697,405 A | 10/1972 | Butter et al. | 204/238 |
| 3,697,406 A | 10/1972 | Svendsen | 204/613 |
| 3,773,648 A | 11/1973 | Van Welzen et al. | 204/615 |
| 3,791,950 A | 2/1974 | Allington | 204/462 |
| 3,902,986 A | 9/1975 | Nees | 204/615 |
| 3,980,546 A | 9/1976 | Caccavo | 204/615 |
| 4,111,785 A | 9/1978 | Roskam | 204/615 |
| 4,326,934 A | 4/1982 | Pohl | 204/547 |
| 4,390,403 A | 6/1983 | Batchelder | 204/547 |
| 4,441,972 A | 4/1984 | Pohl | 204/547 X |
| 4,479,861 A | 10/1984 | Hediger | 204/615 |
| 4,617,102 A * | 10/1986 | Tomblin et al. | 204/613 |
| 4,661,451 A | 4/1987 | Hansen | 435/174 |
| 4,699,706 A | 10/1987 | Burd et al. | 204/613 |
| 4,737,259 A | 4/1988 | Ogawa et al. | 204/606 |
| 4,787,963 A | 11/1988 | MacConnell | 204/450 |
| 4,877,510 A | 10/1989 | Chen | 204/613 |
| 4,908,112 A | 3/1990 | Pace | 210/198.2 |
| 4,936,963 A | 6/1990 | Mandecki et al. | 204/468 |
| 4,971,670 A | 11/1990 | Faupel et al. | 204/459 |
| 5,078,853 A * | 1/1992 | Manning et al. | 204/616 |
| 5,126,022 A | 6/1992 | Soane | 204/458 |
| 5,139,637 A | 8/1992 | MacConnell | 204/466 |
| 5,151,165 A | 9/1992 | Huynh | 204/615 |
| 5,151,189 A | 9/1992 | Hu et al. | 210/635 |
| 5,188,963 A * | 2/1993 | Stapleton | 204/613 X |
| 5,209,831 A | 5/1993 | MacConnell | 204/616 |
| 5,217,593 A | 6/1993 | MacConnell | 204/457 |
| 5,269,931 A | 12/1993 | Hu et al. | 210/635 |
| 5,340,449 A | 8/1994 | Shukla | 204/464 |
| 5,344,535 A | 9/1994 | Betts et al. | 204/547 |
| 5,376,249 A | 12/1994 | Afeyan et al. | 204/452 |
| 5,382,511 A * | 1/1995 | Stapleton | 435/287.2 |
| 5,427,664 A | 6/1995 | Stoer et al. | 204/516 |
| 5,434,049 A | 7/1995 | Okano | 435/6 |
| 5,445,934 A | 8/1995 | Fodor et al. | |
| 5,451,500 A | 9/1995 | Stapleton | 435/6 |
| 5,527,670 A | 6/1996 | Stanley | |
| 5,569,367 A | 10/1996 | Betts et al. | 204/547 |
| 5,589,047 A | 12/1996 | Coster et al. | 204/450 |
| 5,593,580 A | 1/1997 | Kopf | 210/321.72 |
| 5,605,662 A | 2/1997 | Heller et al. | 422/68.1 |
| 5,632,957 A | 5/1997 | Heller et al. | 422/68.1 |
| 5,653,859 A | 8/1997 | Parton et al. | 204/450 |
| 5,653,939 A | 8/1997 | Hollis | |
| 5,674,743 A * | 10/1997 | Ulmer | 435/287.2 |
| 5,728,267 A | 3/1998 | Floherty | 210/321.72 |
| 5,795,457 A | 8/1998 | Pethig et al. | 204/547 |
| 5,814,200 A | 9/1998 | Pethig et al. | 204/547 |
| 5,849,486 A | 12/1998 | Heller et al. | 435/6 |
| 5,856,174 A * | 1/1999 | Lipshutz et al. | 435/286.5 |
| 5,858,192 A | 1/1999 | Becker et al. | 204/547 |
| 6,017,696 A | 1/2000 | Heller | 435/6 |
| 6,048,690 A | 4/2000 | Heller et al. | 435/6 |
| 6,051,380 A | 4/2000 | Sosnowski et al. | 435/6 |
| 6,054,270 A | 4/2000 | Southern | |
| 6,071,394 A | 6/2000 | Cheng et al. | 204/547 |
| 6,099,803 A | 8/2000 | Ackley et al. | 422/68.1 |
| 6,113,768 A | 9/2000 | Fuhr et al. | 204/643 |
| 6,280,590 B1 | 8/2001 | Cheng et al. | 204/463 |
| 6,309,601 B1 | 10/2001 | Juncosa et al. | 422/68.1 |
| 6,335,161 B1 | 1/2002 | Martin et al. | 435/6 |

FOREIGN PATENT DOCUMENTS

| | | |
|---|---|---|
| EP | 0 287 513 | 10/1988 |
| EP | 0 471 949 | 2/1992 |
| EP | 0 544 969 | 6/1993 |
| GB | 2 118 975 A | 11/1983 |
| GB | 1 359 944 | 7/1994 |
| JP | 8021679 | 3/1973 |
| SU | 434985 | 1/1975 |
| SU | 616568 | 7/1978 |
| WO | WO 93/05390 | 3/1993 |
| WO | WO 01/13126 A1 | 2/2001 |

OTHER PUBLICATIONS

Becker et al., "The removal of human leukemia cells from blood using interdigitated microelectrodes," J. Phys. D: Appl. Phys., vol. 27, 1994, 2659–2662.

Cheng, J. et al, "Preparation & Hybridization Analysis Of DNA/RNA From *E.coli* On Microfabricated Bioelectronic Chips", Nature/Biotechnology, vol. 16, 1998, 541–546.

Edman, C.F. et al., "Electric field directed nucleic acid hybridization on microchips", Nucleic Acids Research, vol. 25, No. 24, 1997, 4907–4914.

Fuhr et al., "Positioning and Manipulation of Cells and Microparticles Using Miniaturized Electric Field Traps and Travelling Waves", Sensors and Materials, vol. 7, No. 2, 1995, 131–146.

Fuhr, G., "Cell Manipulation and Cultivation Under AC Electric Field Influence in Highly Conductive Culture Media", Biochem. Biophys. Acta, vol. 1158, 1993, 40–46.

Gilles, P.N., et al, "Single Nucleotide Polymorphic Discrimination By An Electronic Dot Blot Assay On Semiconductor Chips", Nature/Biotechnology, vol. 17, No. 4, 1999, 365–370.

Heller, M.J., "An Active Microelectronics Device For Multiplex Analysis", IEEE Engineering in Medicine & Biology, Mar./Apr. 1996, 100–104.

Huang, Y. et al., "Electric Manipulation Of Bioparticles & Macromolecules On Microfabricated Electrodes", Analytical Chemistry, vol. 73, No. 7, 2001, 1549–1559.

Manz, A., et al, "Miniaturized Total Chemical Analysis System: A Novel Concept For Chemical Sensing", Sensors & Actuators B1, 1990, 244–248.

Markx et al., "Dielectrophoretic characterization and separation of micro–organisms", Microbiology, vol. 140, 1994, 585–591.

Markx et al., "Dielectrophoretic separation of bacteria using a conductivity gradient," Journal of Biotechnology, vol. 51, 1996, 175–180.

Pethig R. et al., "Positive and negative dielectrophoretic collection of colloidal particles using interdigitated castellated mocroelectrodes," J. Phys. D: Appl. Phys, vol. 24, 1992, 881–888.

Pethig, R., "Dielectrophoresis: Using Inhomogeneous AC Electrical Fields to Separate and Manipulate Cells," Critical Reviews in Biotechnology, vol. 16, No. 4, 1996, 331–348.

Scanning Laser Microscopy Lab, Web Site print–out, http://www.science.uwaterloo.ca/research_groups/confocal, 1997.

Sosnowski, R. et al., "Rapid determination of single base mismatch mutations in DNA hybrids by direct electric field control", Proc. Natl. Acad. Sci. USA, vol. 94, Feb. 1997, 1119–1123.

Wang et al., "Dielectrophoretic Manipulation of Particles," IEEE Transactions on Industry Applications, vol. 33, No. 3, May/Jun. 1997, 660–669.

Wang, X., "A Unified Theory of Dielectrophoresis and Travelling Wave Dielectrophoresis", J. Phys. D: Appl. Phys., vol. 27, 1994, 1571–1574.

Washizu, M., "Molecular Dielectrophoresis of Biopolymers", IEEE Trans. Industry Applicat., vol. 30, 1994, 835–843.

Wilson, T and Sheppard, C., "Theory and Practice of Scanning Optical Microscopy", Academic Press, 1984 (ISBN–0–12–757760–2).

* cited by examiner

Figure #18

APPARATUS FOR ACTIVE BIOLOGICAL SAMPLE PREPARATION

This a division of application Ser. No. 08/709,358, filed Sep. 6, 1996 now U.S. Pat. No. 6,129,828. The above application is hereby expressly and fully incorporated herein by reference.

FIELD OF THE INVENTION

This invention relates to devices and methods for performing active, multi-step molecular and biological sample preparation and diagnostic analyses. More particularly, the invention relates to sample preparation, cell selection, biological sample purification, complexity reduction, biological diagnostics and general sample preparation and handling.

BACKGROUND OF THE INVENTION

Molecular biology comprises a wide variety of techniques for the analysis of nucleic acid and protein. Many of these techniques and procedures form the basis of clinical diagnostic assays and tests. These techniques include nucleic acid hybridization analysis, restriction enzyme analysis, genetic sequence analysis, and the separation and purification of nucleic acids and proteins (See, e.g., J. Sambrook, E. F. Fritsch, and T. Maniatis, *Molecular Cloning: A Laboratory Manual*, 2 Ed., Cold spring Harbor Laboratory Press, Cold Spring Harbor, N.Y., 1989).

Most of these techniques involve carrying out numerous operations (e.g., pipetting, centrifugations, electrophoresis) on a large number of samples. They are often complex and time consuming, and generally require a high degree of accuracy. Many a technique is limited in its application by a lack of sensitivity, specificity or reproducibility. For example, these problems have limited many diagnostic applications of nucleic acid hybridization analysis.

The complete process for carrying out a DNA hybridization analysis for a genetic or infectious disease is very involved. Broadly speaking, the complete process may be divided into a number of steps and substeps. In the case of genetic disease diagnosis, the first step involves obtaining the sample (e.g., blood or tissue). Depending on the type of sample, various pre-treatments would be carried out. The second step involves disrupting or lysing the cells, which then releases the crude DNA and RNA (for simplicity, a reference to DNA in the following text also refers to RNA, where appropriate) material along with other cellular constituents. Generally, several sub-steps are necessary to remove cell debris and to purify further the crude lysate. At this point several options exist for further processing and analysis. One option involves denaturing the purified sample DNA and carrying out a direct hybridization analysis in one of many formats (dot blot, microbead, microtiter plate, etc.). A second option, called Southern blot hybridization, involves cleaving DNA with restriction enzymes, separating the DNA fragments on an electrophoretic gel, blotting to a membrane filter, and then hybridizing the blot with specific DNA probe sequences. This procedure effectively reduces the complexity of the genomic DNA sample, and thereby helps to improve the hybridization specificity and sensitivity. Unfortunately, this procedure is long and arduous. A third option is to carry out the polymerase chain reaction (PCR) or other amplification procedure. The PCR procedure amplifies (increases) the number of target DNA sequences. Amplification of target DNA helps to overcome problems related to complexity and sensitivity in analysis of genomic DNA or RNA. All these procedures are time consuming, relatively complicated, and add significantly to the cost of a diagnostic test. After these sample preparation and DNA processing steps, the actual hybridization reaction is performed. Finally, detection and data analysis convert the hybridization event into an analytical result.

The steps of sample preparation and processing have typically been performed separate and apart from the other main steps of hybridization and detection and analysis. Indeed, the various substeps comprising sample preparation and DNA processing have often been performed as a discrete operation separate and apart from the other substeps. Considering these substeps in more detail, samples have been obtained through any number of means, such as obtaining of whole blood, tissue, or other biological fluid samples. In the case of blood, the sample is often processed to remove red blood cells and retain the desired nucleated (white) cells. This process is usually carried out by density gradient centrifugation. Cell disruption or lysis is then carried out, preferably by the technique of sonication, freeze/thawing, or by addition of lysing reagents.

In certain cases, the blood is extensively processed to remove contaminants. One such system known to the prior art is the Qiagen system. This system involves prior lysis followed by digestion with proteinase K, after which the sample is loaded onto a column and then eluted with a high salt buffer (e.g., 1.25 M NaCl). The sample is concentrated by precipitation with isopropanol and then centrifuged to form a pellet. The pellet is then washed with ethanol and centrifuged, after which it is placed in a desired buffer. The total purification time is greater than approximately two hours and the manufacturer claims an optical density ratio (260 nm/280 nm) of 1.7 to 1.9 (OD 260–280). The high salt concentration can preclude performance of certain enzymatic reactions on the prepared materials. Further, DNA prepared by the Qiagen method has relatively poor transport on an electrophoretic diagnostic system using free field electrophoresis.

Returning now to the general discussion of sample preparation, crude DNA is often separated from the cellular debris by a centrifugation step. Prior to hybridization, double-stranded DNA is denatured into single-stranded form. Denaturation of the double-stranded DNA has generally been performed by the techniques involving heating (>Tm), changing salt concentration, addition of base (e.g., NaOH), or denaturing reagents (e.g., urea, formamide). Workers have suggested denaturing DNA into its single-stranded form in an electrochemical cell. The theory is stated to be that there is electron transfer to the DNA at the interface of an electrode, which effectively weakens the double-stranded structure and results in separation of the strands. See, e.g., Stanley, "DNA Denaturation by an Electric Potential", U.K. patent application 2,247,889 published Mar. 18, 1992.

Nucleic acid hybridization analysis generally involves the detection of a very small number of specific target nucleic acids (DNA or RNA) with an excess of probe DNA, among a relatively large amount of complex non-target nucleic acids. DNA complexity is sometimes overcome to some degree by amplification of target nucleic acid sequences using polymerase chain reaction (PCR). (See, M. A. Innis et al, *PCR Protocols: A Guide to Methods and Applications*, Academic Press, 1990). While amplification results in an enormous number of target nucleic acid sequences that improves the subsequent direct probe hybridization step, amplification involves lengthy and cumbersome procedures that typically must be performed on a stand alone basis relative to the other substeps. Complicated and relatively large equipment is required to perform the amplification step.

The actual hybridization reaction represents an important step and occurs near the end of the process. The hybridization step involves exposing the prepared DNA sample to a specific reporter probe, at a set of optimal conditions for hybridization to occur to the target DNA sequence. Hybridization may be performed in any one of a number of formats. For example, multiple sample nucleic acid hybridization analysis can be conducted on a variety of filter and solid support formats (See, G. A. Beltz et al., in *Methods in Enzymology*, Vol. 100, Part B, R. Wu, L. Grossman, K. Moldave, Eds., Academic Press, New York, Chapter 19, pp. 266–308, 1985). One format, the so-called "dot blot" hybridization, involves the non-covalent attachment of target DNAs to a filter, which are subsequently hybridized with a radioisotope labelled probe(s). "Dot blot" hybridization has gained wide-spread use, and many versions have been developed (See, M. L. M. Anderson and B. D. Young, in *Nucleic Acid Hybridization—A Practical Approach*, B. D. Hames and S. J. Higgins, Eds., IRL Press, Washington, D.C. Chapter 4, pp. 73–111, 1985). "Dot blot" assays have been developed for the multiple analysis of genomic mutations (D. Nanibhushan and D. Rabin, in EPA 0228075, Jul. 8, 1987) and for the detection of overlapping clones and the construction of genomic maps (G. A. Evans, in U.S. Pat. No. 5,219,726, Jun. 15, 1993).

New techniques are being developed for carrying out multiple sample nucleic acid hybridization analysis on micro-formatted multiplex or matrix devices (e.g., DNA chips) (See, M. Barinaga, 253 Science, pp. 1489, 1991; W. Bains, 10 Bio/Technology, pp. 757–758, 1992). These methods usually attach specific DNA sequences to very small specific areas of a solid support, such as micro-wells of a DNA chip. These hybridization formats are micro-scale versions of the conventional "dot blot" and "sandwich" hybridization systems.

The micro-formatted hybridization can be used to carry out "sequencing by hybridization" (SBH) (See, M. Barinaga, 253 Science, pp. 1489, 1991; W. Bains, 10 Bio/Technology, pp. 757–758, 1992). SBH makes use of all possible n-nucleotide oligomers (n-mers) to identify n-mers in an unknown DNA sample, which are subsequently aligned by algorithm analysis to produce the DNA sequence (R. Drmanac and R. Crkvenjakov, Yugoslav Patent Application #570/87, 1987; R. Drmanac et al., 4 Genomics, 114, 1989; Strezoska et al., 88 Proc. Natl. Acad. Sci. USA 10089, 1992; and R. Dramanac and R. B. Crkvenjakov, U.S. Pat. No. 5,202,231, Apr. 13, 1993).

There are two formats for carrying out SBH. The first format involves creating an array of all possible n-mers on a support, which is then hybridized with the target sequence. The second format involves attaching the target sequence to a support, which is sequentially probed with all possible n-mers. Both formats have the fundamental problems of direct probe hybridizations and additional difficulties related to multiplex hybridizations.

Southern, United Kingdom Patent Application GB 8810400, 1988; E. M. Southern et al., 13 Genomics 1008, 1992, proposed using the first format to analyze or sequence DNA. Southern identified a known single point mutation using PCR amplified genomic DNA. Southern also described a method for synthesizing an array of oligonucleotides on a solid support for SBH. However, Southern did not address how to achieve an optimal stringency condition for each oligonucleotide on an array.

Concurrently, Drmanac et al., 260 Science 1649–1652, 1993, used the second format to sequence several short (116 bp) DNA sequences. Target DNAs were attached to membrane supports ("dot blot" format). Each filter was sequentially hybridized with 272 labelled 10-mer and 11-mer oligonucleotides. A wide range of stringency conditions was used to achieve specific hybridization for each n-mer probe; washing times varied from 5 minutes to overnight, and temperatures from 0° C. to 16° C. Most probes required 3 hours of washing at 16° C. The filters had to be exposed for 2 to 18 hours in order to detect hybridization signals. The overall false positive hybridization rate was 5% in spite of the simple target sequences, the reduced set of oligomer probes, and the use of the most stringent conditions available.

A variety of methods exist for detection and analysis of hybridization events. Depending on the reporter group (fluorophore, enzyme, radioisotope, etc.) used to label the DNA probe, detection and analysis are carried out fluorometrically, colorimetrically, or by autoradiography. By observing and measuring emitted radiation, such as fluorescent radiation or particle emission, information may be obtained about the hybridization events. Even when detection methods have very Cr high intrinsic sensitivity, detection of hybridization events is difficult because of the background presence of non-specifically bound materials. A number of other factors also reduce the sensitivity and selectivity of DNA hybridization assays.

Attempts have been made to combine certain processing steps or substeps together. For example, various microrobotic systems have been proposed for preparing arrays of DNA probes on a support material. For example, Beattie et al., in *The 1992 San Diego Conference: Genetic Recognition*, November, 1992, used a microrobotic system to deposit micro-droplets containing specific DNA sequences into individual microfabricated sample Wells on a glass substrate. Various attempts have been made to describe integrated systems formed on a single chip or substrate, wherein multiple steps of an overall sample preparation and diagnostic system would be included. For example, A. Manz et al., in "Miniaturized Total Chemical Analysis System: A Novel Concept For Chemical Sensing", *Sensors And Actuators*, B1(1990), pp. 244–248, describe a 'total chemical analysis system' (TAS) which comprises a modular construction of a miniaturized total chemical analysis system. Sampling, sample transport, any necessary chemical reactions, chromatographic separations as well as detection were to be automatically carried out. Yet another proposed integrated system is Stapleton, U.S. Pat. No. 5,451,500, which describes a system for the automated detection of target nucleic acid sequences in which multiple biological samples are individually incorporated into matrices containing carriers in a 2-dimensional format. Different types of carriers are described for different kinds of diagnostic tests or test panels.

Various multiple electrode systems are disclosed which purport to perform multiple aspects of biological sample preparation or analysis. Pace, U.S. Pat. No. 4,908,112, entitled "Silicon Semiconductor Wafer for Analyzing Micronic Biological Samples" describes an analytical separation device in which a capillary-sized conduit is formed by a channel in a semiconductor device, wherein electrodes are positioned in the channel to activate motion of liquids through the conduit. Pace states that the dimension transverse to the conduit is less than 100 $\mu$m. Pace states that all functions of an analytical instrument may be integrated within a single silicon wafer: sample injection, reagent introduction, purification, detection, signal conditioning circuitry, logic and on-board intelligence. Soane et al., in U.S. Pat. No. 5,126,022, entitled "Method and Device for Moving Molecules by the Application of a Plurality of Electrical Fields", describes a system by which materials are moved through trenches by application of electric potentials to electrodes in which selected components may be guided to various trenches filled with antigen-antibodies reactive with given charged particles being moved in the medium or moved into contact with complementary components, dyes, fluorescent tags, radiolabels, enzyme-specific tags or other types of chemicals for any number of purposes such as various transformations which are either physical or chemical in nature. It is said that bacterial or mammalian cells, or viruses may be sorted by complicated trench networks by application of potentials to electrodes where movement through the trench network of the cells or viruses by application of the fields is based upon the size, charge or shape of the particular material being moved. Clark, U.S. Pat. No. 5,194,133, entitled "Sensor Devices", discloses a sensor device for the analysis of a sample fluid which includes a substrate in a surface of which is formed an elongate micro-machined channel containing a material, such as starch, agarose, alginate, carrageenan or polyacrylamide polymer gel, for causing separation of the sample fluid as the fluid passes along the channel. The biological material may comprise, for example, a binding protein, an antibody, a lectin, an enzyme, a sequence of enzymes or a lipid.

Various devices for eluting DNA from various surfaces are known. Shukla U.S. Pat. No. 5,340,449, entitled "Apparatus for Electroelution" describes a system and method for the elution of macromolecules such as proteins, DNA and RNA from solid phase matrix materials such as polyacrylamide, agarose and membranes such as PVDF in an electric field. Materials are eluted from the solid phase into a volume defined in part by molecular weight cut-off membranes. Okano, U.S. Pat. No. 5,434,049, entitled "Separation of Polynucleotides Using Supports Having a Plurality of Electrode-Containing Cells" discloses a method for detecting a plurality of target polynucleotides in a sample, the method including the step of applying a potential to individual chambers so as to serve as electrodes to elute captured target polynucleotides, the eluted material then available for collection.

Generally, the prior art processes have been extremely labor and time intensive. For example, the PCR amplification process is time consuming and adds cost to the diagnostic assay. Multiple steps requiring human intervention either during the process or between processes is suboptimal in that there is a possibility of contamination and operator error. Further, the use of multiple machines or complicated robotic systems for performing the individual processes is often prohibitive except for the largest laboratories, both in terms of the expense and physical space requirements.

As is apparent from the preceding discussion, numerous attempts have been made to provide effective techniques to conduct sample preparation reactions. However, for the reasons stated above, these techniques are limited and lacking. These various approaches are not easily combined to form a system which can carry out a complete DNA diagnostic assay. Despite the long-recognized need for such a system, no satisfactory solution has been proposed previously.

SUMMARY OF THE INVENTION

This invention relates broadly to the methods and apparatus for electronic sample preparation of biological materials for their ultimate use in diagnosis or analysis. An integrated system is provided for performing some or all of the processes of: receipt of biological materials, cell selection, sample purification, complexity reduction and/or diagnosis and analysis. Separation of desired components, such as DNA, RNA or proteins from crude mixtures such as biological materials or cell lysates. Electronic sample preparation utilizes the differential mobility and/or differential affinity for various materials in the sample for purposes of preparation and separation. These methods and apparatus are especially useful for the free field electrophoretic purification of DNA from a crude mixture or lysate. In one aspect of this invention, a device comprises at least a first central or sample chamber adapted to receive a buffer solution and a second central or sample chamber adapted to receive a same or different buffer solution, where the first sample chamber and the second sample chamber are separated by a spacer region which preferably includes a trap, membrane or other affinity material. A first electrode in electrical contact with the conductive solution of the first sample chamber and a second electrode in electrical contact with the conductive solution of the second sample chamber are provided. Preferably, each electrode is contained within its own electrode chamber, the electrode chamber being separated from the corresponding sample chamber via a protective layer or separation medium, e.g., a membrane, such as an ultrafiltration membrane, a polymer or a gel. In operation, the sample mixture is placed within the first central chamber. The central chambers contain a solution, preferably a low conductivity buffer solution, such as 50 mM histidine, 250 mM HEPES, or 0.5×TBE. A mixture of biological substances, for example a crude lysate, is added to the first chamber and then the electrodes are activated. Substances with mobility in an electric field will move towards one electrode or the other depending on the charge of the substance. In one embodiment, the desired and undesired substances with similar charges will be attracted to an electrode biased with the opposite charge to the desired substance, located in the second chamber. Therefore, the desired substance and the undesired substances of similar charge will move towards the affinity material which is between the first and second chambers.

In one embodiment, the sample mixture is composed of a desired substance which has charge mixed with undesired substances some of which have charges. After the electrodes are activated, the desired substance travels toward the second chamber where the electrode, biased with opposite charge, is located and binds to the affinity material. In contrast, the similarly charged, undesired substances move toward the electrode biased with the opposite charge and pass through the affinity material into the second chamber. Other undesired substances with the opposite charge will be attracted toward the electrode in the first chamber. After the undesired substances have passed through the affinity material, the electrolyte solution may be changed in both chambers to remove the undesired substances. Then the desired substance is eluted into the fresh electrolyte solution. Elution can be accomplished by continued electrophoresis at the same or increased current or by the addition of a chemical, such as a detergent, salt, a base or an acid, that will cause elution from the affinity material. In addition, a change in temperature could be used to elute the desired substance.

In one particular embodiment, the affinity material is composed of a gel with sufficient volume to hold a substantial fraction, e.g., preferably 50%, and more preferably, 80%, of the desired substance in the sample. The gel composition and concentration is chosen such that the mobility of the desired substance which has high molecular weight (30,000 to 3,000,000 daltons) is retarded by the gel but the mobility of the undesired substances which have low molecular weight (100 to 10,000 daltons) is relatively unaffected. Consequently, the gel will release the desired substance only after a longer period of electrophoresis or a higher current than is necessary for the passage of the undesired substances. In effect the gel is a trap for the desired substance but does not provide a relatively significant barrier to undesired substances. The desired and undesired substances preferably have a very large difference in electrophoretic mobility while traveling through the gel for the gel to serve as a trap. Preferably, the trap does not effectively resolve mobility differences among fragments which have similar compositions and molecular weights which are within a factor of substantially 10 of each other.

In accordance with this invention, the resolution of different molecular weights is preferentially sacrificed in favor of rapid mobility. Preferably, the gel in the device is relatively compact (e.g., 0.5 to 10 mm) in the direction of migration to permit rapid electrophoretic transport. Thus, the speed of this technique is not compatible with conventional resolution of substances by size except between substances with very gross differences in size. Consequently, it is inherent in this technique that desired substances of very different molecular weights will be copurified. The preparation of substances of similar composition but different sizes may be advantageous to the user as for example in the purification of DNA of different sizes for the purpose of cloning of a whole or representative portion of a genome of an organism.

In accordance with one aspect of this invention, the desired substance is propelled into and out of the gel in the same device. That is, in the preferred embodiment, different regions within the whole system serve as traps and therefore, help to separate analytes or materials to be eluted. The integration of electrophoresis and elution steps also provides significant advantages for the user in saving time, reducing the number of steps required and decreasing the amount of space required for the apparatus.

In one aspect of the invention, a device containing multiple electrode chambers in electrical communication with a first and second end sample chamber and one or more intermediate sample chambers is advantageously utilized. In the preferred embodiment, each of the end sample chambers and the intermediate sample chamber or chambers is in electrical communication with an electrode chamber, preferably having the sample chamber separated from the electrode chamber by a membrane. Preferably, the electrode chamber has a buffer volume which is larger than and preferably much larger than (e.g., at least 10 to 1) the volume of the sample which is loaded into the sample chamber.

In another aspect of this invention, the traps, membranes or other affinity materials serve as a transporter or 'dipstick' to collect and permit transport of materials. In one embodiment of this device, the membrane or other affinity material disposed between adjacent sample chambers is provided with structural integrity to permit the removal of the trap or affinity material from the chamber structures. In one preferred embodiment, a membrane or trap is held in a frame which is adapted to mate with a channel formed at the spacer region. The transporter or dipstick may be utilized to transport the collected material for further processing, such as further purification, complexity reduction or assaying or diagnosis. Optionally, the transporter may be disposed adjacent to or formed in electrical communication with a power source.

In yet another aspect of this invention, first and second electrodes are disposed within an intervening sample solution, the system further including a third electrode between the first and second electrodes. The third electrode may serve as a control electrode to modulate the flow of charged materials within the sample solution. The third electrode is preferably formed as a grid, and may be advantageously formed by sputtering a metal coating on a membrane. The third electrode, or grid, is preferably disposed within the sample solution closer to the first electrode than the second electrode. In one mode of operation, a sample is placed within the sample solution between the first and third electrodes, and the first and second electrodes are biased for net migration of charged materials of a first charge toward the second electrode. The third electrode or grid is preferably biased slightly negative or neutral. Once the desired DNA or other charged materials passes through or by the third electrode or grid, the third electrode or grid is preferably made relatively negative. This increased negativity serves to move the negatively charged DNA towards the second electrode, and to repel other, more slowly moving negatively charged materials which still remain between the first electrode and the third or grid electrode.

In yet another aspect of this invention, a pair of electrodes are located within a sample solution and are operated so as to bunch or concentrate a subset of the charged macromolecules within the sample solution. Biasing one electrode so as to accelerate motion of charged macromolecules towards the other electrode, and biasing the other electrode so as to retard motion of the charged macromolecules which are closer to that electrode in the region between the electrodes. Such bunching serves to physically concentrate the charged macromolecules within the region.

In a preferred embodiment, a "C" shaped electrode is utilized. This structure serves to bunch materials contained within the region bounded by the C-shaped electrode, as well as to repel like charged materials which are external to the region bounded by the C-shaped region. Further, the materials contained within the C-shaped region are subject to a force in a sideways (i.e., a transverse or oblique direction to the net flow direction apart from the C-shaped electrode). The C-shaped electrode may be an integrated, continuous electrode or may be segmented. Other shapes are advantageously utilized, such as parabolic structures. The C-shaped region is sized to include within the region the desired or target material.

A complexity reduction device includes one or more probe areas which comprise a support material, preferably a polymer gel, such as an agarose, acrylamide or other conductive polymer, to which capture probes are attached. The support material is formed in contact with an electrode to permit the electrophoretic attraction and hybridization of the capture probes with the target materials. Electrical elution or electronic stringency control of the captured materials may be used. In one embodiment, the complexity reduction device is formed from the combination of a chamber mated to a printed circuit board. The chamber includes vias in which the support material is located. The printed circuit board preferably including concentric vias to provide a continuous space for the inclusion of the support material. In this embodiment, gases or other reaction products may be vented through the via, in part because the gas generally does not rise into the via since it is filled with polymer. Therefore, these gases or other reaction products do not come in contact with the analytes, such as DNA. The complexity reduction system optionally may further include disposal regions for the attraction and/or disposal of undesired materials. The disposal regions include an electrode in electrical communication through the conductive polymer. In operation, the complexity reduction device performs free field electrophoretic transport. Alternatively, an uncovered electrode in contact with the solution may be utilized for disposal of undesired materials.

In yet another aspect of this invention, a DNA or other nucleic acid purification device is provided. An upper reservoir containing an electrode, which may be identified as a cathode, is adapted to receive a buffer solution and a sample solution. Preferably, the upstream reservoir includes a tube in fluid communication with the upstream reservoir, the tube having an internal diameter less than the diameter of the upstream reservoir. The tube includes at least a first differential mobility section, preferably a gel, which provides a plug or trap region within the tube. Optionally, the gel may be cast on top of a support membrane. A collection chamber is adjacent to the differential mobility region. In the preferred embodiment, the collection region has a smaller volume than the differential mobility region and is smaller than the sample volume. The reduction in volume from sample to collection permits an increase in volume concentration of DNA and exchanges the DNA into the desired buffer formulation of known volume. An anode is provided in a lower reservoir. In yet another aspect of this invention, the format and transport of DNA is in the horizontal plane instead of vertical.

In operation, a sample is subject to a cell lysing and shearing pre-preparation step. Preferably, the proteins are then reduced in size, such as through application of a proteinase, such as proteinase K. Preferably, when the unit is operated in a vertical format, sucrose or other densifier is added to the sample. The densifier serves to collect and concentrate the sample in a region immediately above the first differential mobility section. The prepared sample including densifier is then injected onto the separation unit in the tube, in a region immediately upstream of the differential mobility region. The cathode and anode are then energized to provide electrophoretic transport of the charged materials within the system, causing the reduced size protein materials to pass through the differential separation medium first, while retaining the relatively slower moving DNA, as well as resulting in the proteinase K or other positively charged materials being removed to the cathode. After a time sufficient to permit desired amounts of protein to pass through the differential mobility region and support membrane, the DNA is eluted from the differential movement region into the sample chamber. Optionally, the buffer solution in the lower reservoir which received the proteinaceous material having passed through the support membrane may be removed and replaced with new buffer solution, and optionally provided with a membrane which serves to retain eluted DNA within the sample chamber.

In yet another aspect of this invention, the cathode and anode electrodes are in communication with the sample through conductive fluids or gel or polymers, but are resident in the power supply or other controlling instrumentation. Conduction is made through fluidic ports and the electrode (noble metal) preferably is not a part of the consumable device.

Integrated systems may be advantageously formed which include some or all of the functions of cell separation, purification, complexity reduction and diagnostics. In one embodiment, a purification chamber includes an input port and multiple electrodes for providing an electrophoretic driving force to the charged materials. A protein trap disposed between the sample input port and an outlet tap serves to trap undesired proteins or other charged macromolecules. In an alternative embodiment, the undesired materials such as proteins are reduced in size or modified in charge so as to increase their degree of mobility relative to the desired materials, such as DNA. The materials for further processing are then removed from the trap or other transportation device for further processing, such as complexity reduction and/or diagnostic procedures. This separation of target materials from the undesired material is accomplished by modifying the electric field to steer the target materials into a region of higher purity (e.g., pure buffer). Electric field modification can be implemented through C-shape electrodes or activation of a new configuration of electrodes which favorably influence the direction of mobility of the target.

In yet another aspect of this invention, an integrated sample preparation, complexity reduction and diagnostic system is provided. An input port receives crude lysate including proteins which have been reduced in size, such as through use of a proteinase. The materials pass through a DNA trap, in which the DNA moves relatively slower than the proteins. The proteins arrive at a protein trap electrophoretically prior to the arrival of the DNA. The DNA then exit the DNA trap towards a collections chamber. Preferably, the collection chamber has a volume which is less than, preferably substantially less than the volume of the DNA trap, such as 50 microliters. This volume is in communication with the complexity reduction and diagnostic chamber. In one aspect of this invention, fluidic transport within the device is accomplished by input ports located at each end of the collection chamber. These dual input ports are adapted to receive any fluid, such as a buffer, an air slug or a reagent. By selective operation of supplies or pumps, the materials contained within the collection chamber e.g., substantially purified DNA, may be forced from the chamber to the complexity reduction device. By utilization of air slugs, various liquids may be separated from one another. By operation of the input liquids or gas, a hydraulic or pneumatic ram serves to move materials within the fluid section of the device. While materials may be pushed forward throughout the system, such as from the collection volume to the complexity reduction to the diagnostic region, the materials may be moved in the opposite direction, e.g., from the complexity reduction chamber to the concentration region.

Accordingly, it is an object of this invention to provide for a sample preparation system useful for biological sample preparation.

It is yet a further object of this invention to provide a system for purification of DNA from biological materials or other crude samples.

It is yet a further object of this invention to provide methods for the separation and purification of desired biological charged macromolecules through differential solution phase mobility and/or differential affinity.

BRIEF DESCRIPTION OF THE DRAWINGS

FIG. 14A shows a cross-sectional view along the line A–A' of FIG. 14.

DETAILED DESCRIPTION OF THE INVENTION

Figure 1:
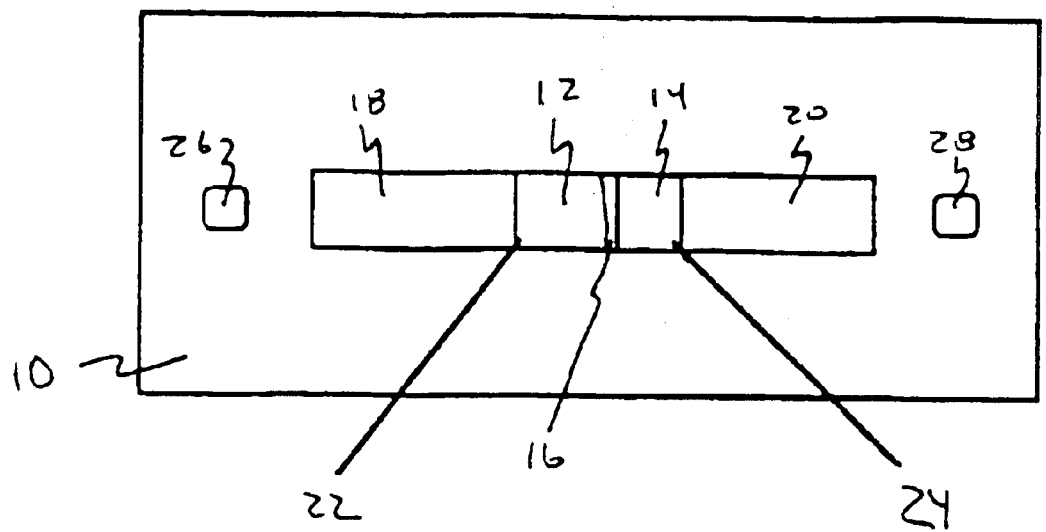
FIG. 1 is a top, plan view of a multiple sample chamber, multiple electrode chamber device.

FIG. 1 shows a top down, plan view of one embodiment of this invention. A frame 10 supports a first central or sample chamber 12 and a second central or sample chamber 14. The designations first and second are arbitrary, and may be reversed, or the chambers may be referred to as the left central chamber 12 and right central chamber 14. Disposed between the left central chamber 12 and right central chamber 14 is a spacer region 16. The spacer region is adapted to receive a trap, membrane or other affinity material or material for relative differentiation of biological materials within the spacer region 16. In one aspect, the spacer region 16 may be filled with a gel cast in the region of the spacer 16 or a membrane may be disposed covering the spacer region 16. Adjacent to the left central chamber 12 is a first electrode chamber 18. The electrode chamber 18 is separated from the central chamber 12 by a membrane 22, preferably an ultrafiltration membrane, most preferably a cellulose acetate membrane. Similarly, a right or second electrode chamber 20 is disposed adjacent to the right central chamber 14, separated by a 133 membrane 24. A function of the membranes 22, 24 is to reduce or prevent contact of the sample materials or selected components thereof from directly contacting the electrodes 26, 28. A first electrode 26 and a second electrode 28 are disposed in contact with the first electrode chamber 18 and second electrode chamber 20, respectively. The electrodes are preferably formed of a noble metal, most especially platinum.

In the preferred embodiment, the frame 10 is formed of a relatively rigid support material which is non-reactive with the materials placed in contact with it. Desired materials include: polymethacrylate, plastics, polyproplene, polycarbonate, PTFE, TEFLON™ or other non-reactive materials. Generally, the frame materials are non-reactive, non-interactive or non-binding with the sample materials. The frame 10 may have formed within it regions comprising the electrode chambers 18, 20, central chambers 12, 14 and the spacer region 16. In one embodiment, the electrode chambers 18, 20, are 0.4 cm wide, 0.6 cm deep and 5 cm long (the direction parallel to a line between the first electrode 26 and second electrode 28). The central chambers 12, 14 have the same width and depth as the electrode chambers 18, 20 and are 1.5 cm long. The spacer region 16 has the same width and depth as the chamber components. 12, 14, 18 and 20, and is 0.4 cm long. Generally, the volume of the spacer region 16 is small relative to the volume of the central chamber 12, 14. Preferably, the volume of the spacer region 16 is less than 50%, and more preferably less than 30% of the volume of the central chamber 12, 14. The embodiment described above as a spacer region 16 with a volume of approximately 25% of that of the central chamber 12, 14. As an alternative measure, the spacer region 16 may be characterized by its distance along the direction the direction from the first electrode 26 to the second electrode 28. Preferably, the linear distance is less than 5 mm, more preferably 4 mm or less, and often in the range of 1–2 mm. In yet another characterization, the thickness of the spacer region 16 in a direction between the first electrode 26 and the second electrode 28 is short relative to the distance between the first electrode 26 and second electrode 28. Preferably, this length is less than 20%, more preferably less than 10% and most preferably less than approximately 5%. Preferably, the size of the spacer region 16 is such, relative to the other structures of the device, that the desired materials may be separated from the undesired materials, so as to permit isolation of the desired materials.

The spacer region 16 includes a material which serves to discriminate amongst macromolecules within the device. One class of materials would comprise protein traps, materials such as PVDF, nitrocellulose and hydrophobic materials. Yet another class of materials are negatively charged materials. Yet a third class of materials are positively charged materials. A modified class of materials utilizes a detergent in combination with the trap which permits the DNA to pass through the trap. Various other surfactants, detergents and materials which achieve the functions of the trap to differentiate amongst materials may be utilized as known to those skilled in the art. DNA/RNA traps would especially include low density polymers (e.g., 0.5–3% agarose, or 5%–15% acrylamide) and PVDF. The latter material is a material which traps DNA to some extent, but from which DNA or RNA may be selectively eluted by adding a detergent.

The electrode chambers 18, 20 and central chambers 12, 14 are filled with a buffer solution. Preferably, the buffer solution is a relatively low conductivity buffer solution. Other functional characteristics of the buffer may include:

chemically low reactivity, Zwitterionic or ampholytes with no net charge. The application entitled "Methods and Materials for Optimization of Electronic Hybridization Reactions", filed on the same date as the instant application, and incorporated herein by reference more fully describes such techniques. Examples of buffers which are suitably acceptable for separation of DNA include: histidine, especially about 50 millimolar histidine, HEPES and 0.5 X TBE. HEPES is 4(-2-Hydroxyethyl)-1-Piperazine Ethanesulfonic acid. TAE is prepared by diluting 10×TAE (0.4 M Tris Acetate, 0.1 M EDTA, 0.2 M glacial acetic acid pH 8.4) 1 to 10 in deionized water. 0.5×TBE is prepared by diluting TBE (0.89M Tris-Borate, 0.89 M Boric Acid, 0.02 M EDTA, pH 8.0) 1 to 20 in deionized water.

In operation, a sample is placed in a central chamber 12, 14, for purposes of discussion assumed to be the left central chamber 12. A potential is applied across the first electrode 26 and second electrode 28, permitting a current to flow through the electrode chambers 18, 20 and central chambers 12, 14. The charged macromolecules in the sample are electrophoretically moved through the left central chamber 12, towards the spacer region 16. If the spacer region 16 includes a protein trap, the DNA is moved through the spacer region 16 into the right central chamber 14. Alternatively, if the spacer region 16 includes a material designed to hold the DNA, but pass the proteins and other undesired materials, the DNA remains on the left portion of the spacer region 16, from which it may be eluted. In the later mode of operation, the buffer in the left central chamber 12 may be replaced prior to eluting the DNA back into the left central chamber 12.

Broadly, the method of this invention provides for active biological sample preparation of a sample comprising a collection of materials including desired materials and undesired materials having differential charge-to-mass ratios, the separation being achieved in an electrophoretic system including solution phase regions and at least one trap region having differential effect on desired materials as compared to undesired materials. The differential effect of the trap region is a function of the physical size, composition and structure of the trap, which are selected so as to selectively retain or pass either the desired or undesired material. In the preferred embodiment, the method includes the step of providing the sample materials to a first sample chamber of the device. Subsequently, the sample is electrophoresed within the system to affect net differential migration between the desired material and the undesired material whereby one of the desired or undesired materials is located within the trap and the other material is in a sample chamber that is, either the desired materials are substantially retained (e.g., preferably $\geq 50\%$, and more preferably, $\geq 80\%$) in the trap, and the undesired materials are substantially not retained in the trap, or vice versa. Subsequently, the desired material are removed from the system, whereby relatively purified desired materials are prepared. If the desired materials are the bound or trapped materials, they may be removed in any number of ways, including but not limited to physical removal from the system, such as by a dipstick, subsequent removal into a fluid or other medium, such as by moving through the trap or moving back into the chamber from which they came, especially if the buffer solution has been changed within that chamber.

Figure 2:
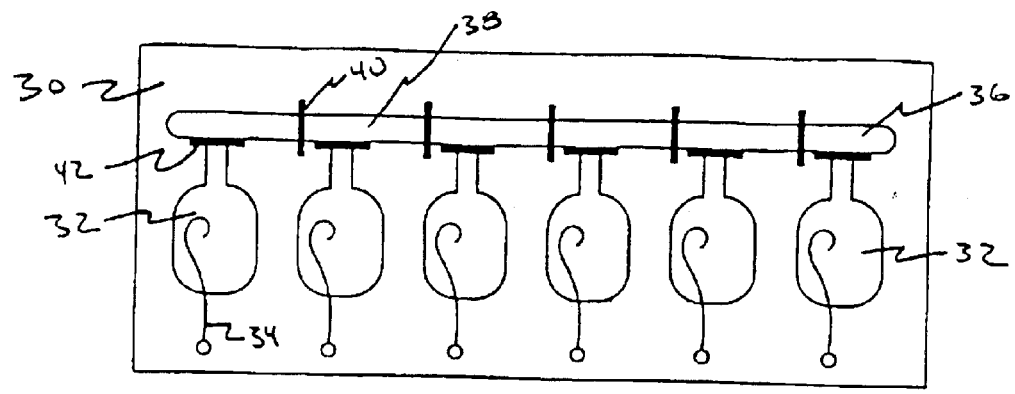
FIG. 2 is a top, plan view of a device including multiple electrode chambers, end sample chambers and multiple intermediate sample chambers.

FIG. 2 shows a plan view of a multichamber arrangement. A frame 30 includes multiple electrode chambers 32. Each electrode chamber 32 includes an electrode 34. Preferably, the electrode is formed of a noble metal, such as platinum, and may be placed in electrical contact with a buffer solution placed within the electrode chamber 32. End sample chambers 36 sandwich one or more intermediate sample chambers 38. The end sample chamber 36 is separated from the adjacent intermediate sample chamber 38 by a separator 40. The separator 40 may comprise an affinity media, a membrane, or other material which selectively differentiates between passage or affinity for various biological materials. The sample chambers 36, 38 are separated from the electrode chamber 32 by a membrane 42. Preferably, the volume of the electrode chamber 32 is larger, preferably a factor of 10 times, and most preferably a factor of 20 times, relative to the size of the sample chamber 36, 38. This is so since electrosmosis through the membrane 42 may result in liquid-level differences. Further, this relatively large volume ratio minimizes the ion concentration gradient between the adjacent electrode chamber 32 and sample chamber 36, 38 and provides a larger buffering capacity around the electrode 34 which increases pH stability which, in turn, optimizes the working time and power (V×I) input to the sample before the detrimental effects of the electrophoretically driven osmosis begin to dominate and negatively impact the process. Yet another object of the relatively large electrode chamber 32 is that adequate spatial separation between the chamber membrane 42 and the electrode 34 is provided so as to prevent bubble attachment to the membrane 42, after the bubbles are formed at the electrode 34. It is desirable to avoid bubble contact with the membrane 42 as they obstruct the membrane and prevent conduction through them, and the bubbles may have large pHs. Further, it is desirable that the electrodes 34 have relatively large surface area, e.g., 5–20 $mm^2$ which minimize bubble formation by reducing local current density near the electrode surfaces and the inherent surface nucleation sites.

The frame 30 may be formed of any material which is non-reactive with the materials to be placed in contact with it. Preferably, the materials are selected to have low autofluorescence at 380 nmUV, and between 480 nm and 630 nm, in order to minimize background signal during quantitation. The sample chambers 36, 38 may be of different sizes. Preferably, the sample chamber 36, 38 is in the range from 300 $\mu$l to 3 ml, most preferably 1 ml. After purification steps, the relatively purified material may be reduced in sample volume, and the volume may be on the order of tens of microliters or less.

Figure 3:
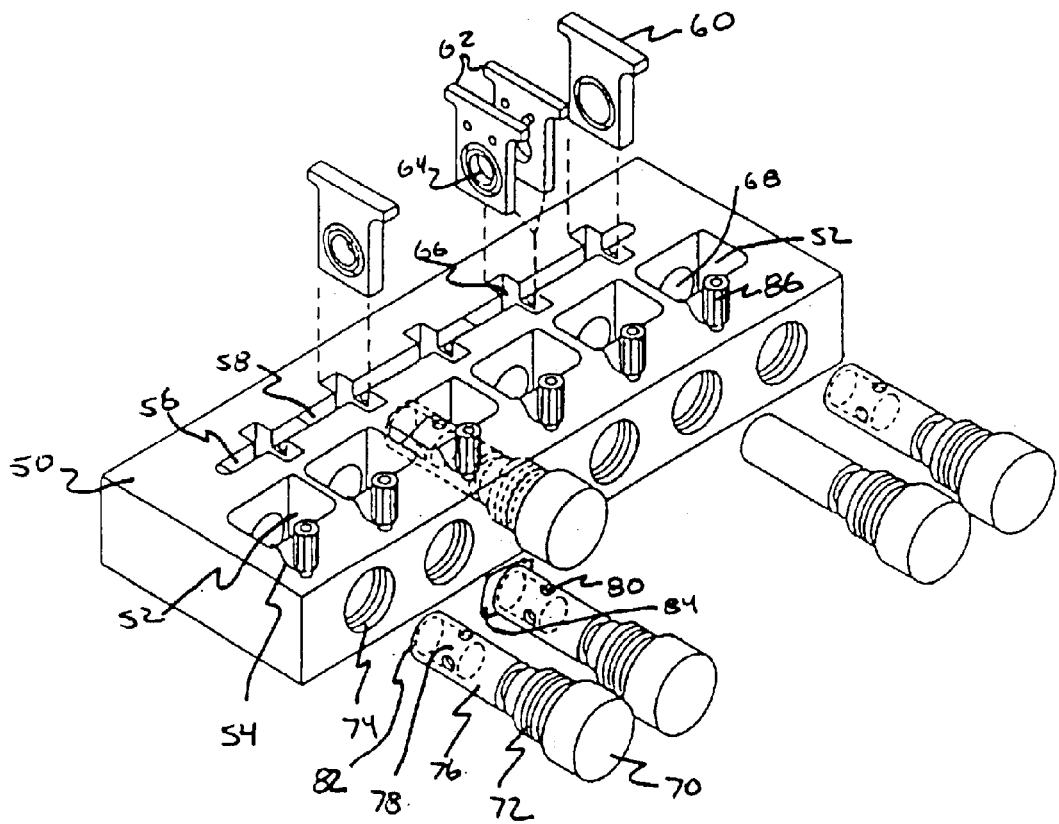
FIG. 3 is a perspective, exploded view of one embodiment of the invention.

FIG. 3 shows a perspective, exploded view of a multi-chamber device. A frame 50 has formed, such as by milling or molding, one or more end sample chambers 56, sample chambers 58 and electrode chambers 52 having the functions and sizes described in connection with FIG. 2. The electrode 54 preferably exits the electrode chamber 52 and is connected via a connector 86, such as a threaded connector as is known to those skilled in the art. Adjacent sample chambers 56, 58 are separated by a membrane holder 60. The membrane holder 60 optionally is formed of membrane holder halves 62 connected via connector 66. An opening 64 in the membrane holder 66. An opening 64 in the membrane holder 60 is adapted to receive a material which differentiates or discriminates the passage of biological materials, such as a membrane or affinity material. The membrane holder 60 is adapted to matingly engage with holder 66. The sample chamber 56, 58 is in communication with the electrode chamber 52 via passage 68. In this embodiment, insert 70 threadingly engages with the frame 50 by threading 72 in receptive threading 74. A barrel 76 includes a counterbore 78 and includes holes 80 to permit passage from the electrode chamber 52 through the holes 80, through the counterbore 78, to the sample chamber 56, 58. The insert 70 preferably terminates at a ring 82, opposite the threaded end of the insert 70, where the ring 82 is adapted to sandwich a filter or membrane 84 between the ring 82 and the bore 68 of the electrode chamber 52. The size of the sample chambers 56, 58 may vary from one to another. Further, the various membrane holders 60 may be utilized, or not, providing yet an additional degree of flexibility in determining the size of the sample chamber 56, 58.

The membrane holder 60 is removable from the frame 50. The membrane holder 60 may include membrane, mesh or beads with functional groups covalently linked to oligonucleotides. After material is captured within the opening 64 of the membrane holder 60, the membrane holder 60 may be removed from the frame 50 and the materials transported to another site.

Figure 4:
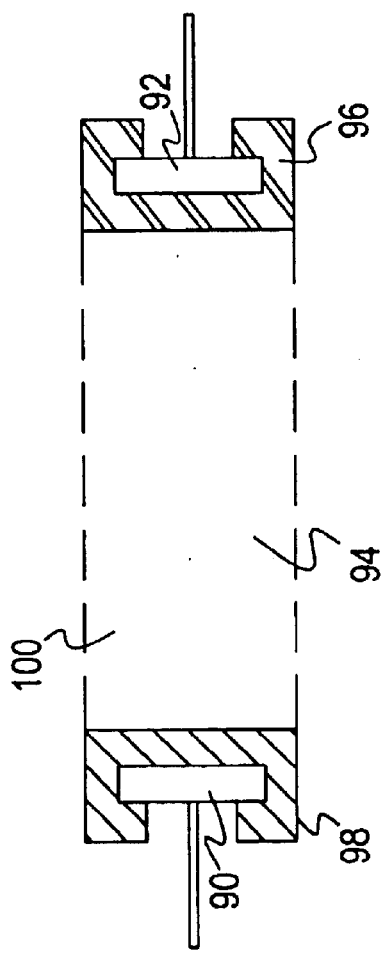
FIG. 4 is a cross-sectional view of a multiple electrode embodiment.

FIG. 4 shows a cross-sectional view of an embodiment of this invention. A first or left electrode 90 and a second or right electrode 92 are adapted to provide an electrophoretic force on charged macromolecules disposed within the solution phase region 94. The solution phase region 94 is shown with a dashed boundary, the physical boundary of which may be formed through any desired support medium not inconsistent with the materials or methods to be achieved with this invention. A trap 96 is disposed at, near or substantially surrounding the second electrode 92. The trap 96 may be formed of the materials, and have the attributes as described for the trap or spacer materials, above. Optionally, a protective or permeable layer 98 is disposed between at least a portion of the solution phase region 94 and the first or right electrode 90. As shown in FIG. 4, the permeable layer 98 serves to block the solution phase region 94 from direct contact with the left electrode 90. In operation, a sample is placed in an input region 100, such as through a port or other opening in the device. The solution phase region 94 contains a buffer or other suitable transport medium, comprised of or having the functions described for the solution phase, above. A sample initially placed in the input region 100 is electrophoretically moved towards the trap 96 by application of potential to the electrodes 90, 92. When the desired material, e.g., DNA, contacts the trap 96, the system is then operated so as to remove the now trapped materials. This could be by removal of the trap 96 from the system, or by eluting the trapped material from the trap 96 back into the solution phase region 94. Preferably, the elution of the trapped material into the solution phase region 94 is preceded by replacing the solution in the solution phase region 94 with a new solution. The solution may be the same or different from that previously existing.

Figure 5:
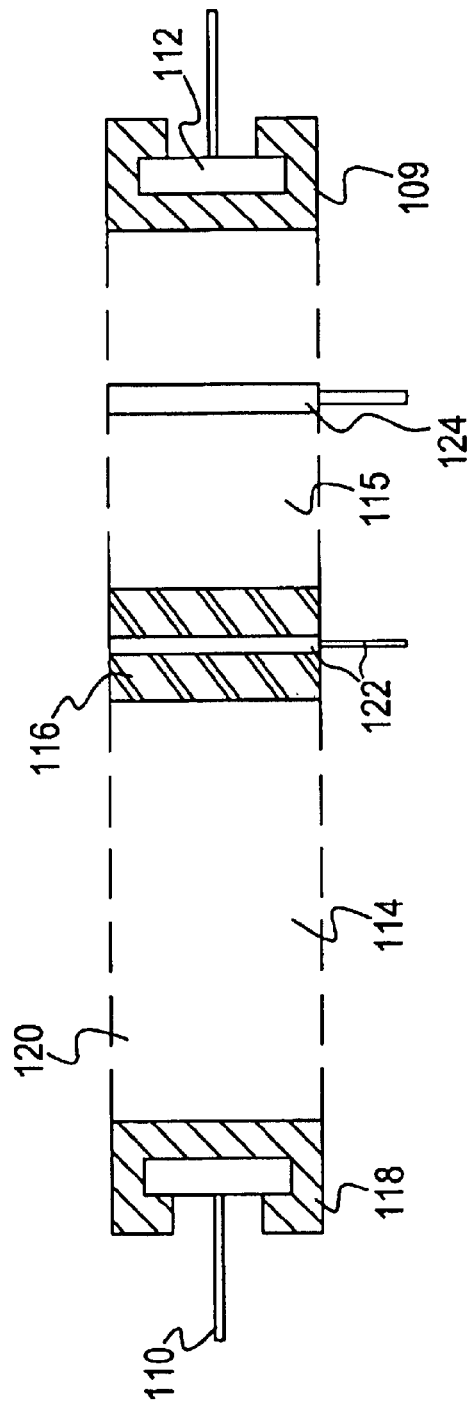
FIG. 5 is a cross-sectional view of a multiple electrode embodiment including a trap electrode.

FIG. 5 shows a cross-sectional view of an alternate embodiment of the invention. A first electrode 110 and a second electrode 112 provide overall electrophoretic movement of charged materials within the first solution phase region 114 and second solution phase region 115. The first electrode 110 optionally has a first permeable layer 118 disposed at, near or substantially around the first electrode 110, so as to minimize contact of the charged macromolecules with the first electrode 110. A second layer 109 is formed at, near or substantially surrounding the second electrode 112. In one version, the second layer 109 comprises a trap, the materials and functionality being those described above. Alternatively, the second layer 109 may comprise a second permeable layer, adapted principally for the protection of charge macromolecules from directly contacting the second electrode 112. Optionally, a trap electrode 122 is located between the first electrode 110 and the second electrode 112, dividing the solution phase region into a first solution phase region 114 and a second solution phase region 115. Further, optionally, the trap electrode 122 may include a trap 116 formed at or integral with the trap electrode 122. In operation, a sample is provided to the input region 120, which, under operation of the electric fields created via the first electrode 110, second electrode 112 and trap electrode 122 cause the electrophoretic movement of the charged macromolecules. Optionally, an additional electrode may be located within the solution phase regions 114, 115.

Figure 6:
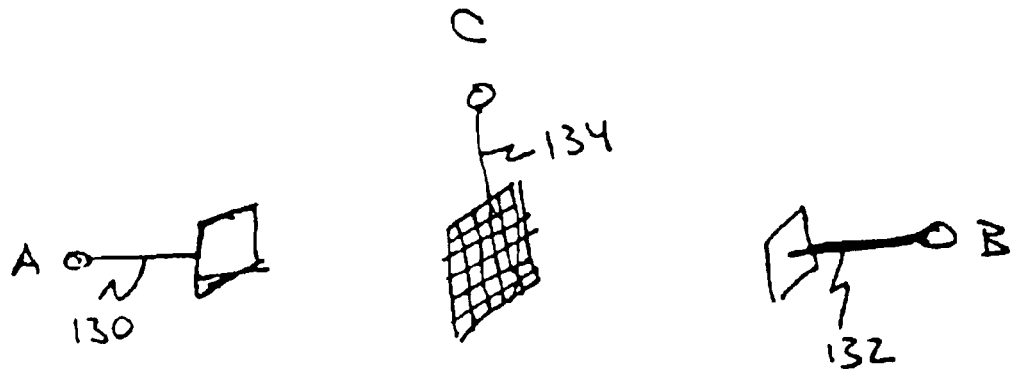
FIG. 6 is a perspective view of a multiple electrode structure including a grid or control electrode.

FIG. 6 shows a perspective view of a first electrode 130, a second electrode 132 and a control electrode 134. Generally, the first electrode 130 may be identified as the cathode and the second electrode 132 the anode, though those terms may be interchanged depending on the polarity of the connections. The control electrode 134 may be spaced equidistant between the first electrode 130 and second electrode 132, though optionally it may be placed closer to the electrodes 130, 132, most preferably to the cathode 130. Variation of the potential applied to the control electrode 134 may be used to modulate the flow of charged macromolecules within the region between the first electrode 130 and second electrode 132. In one mode of operation, the sample is placed between the first electrode 130, the cathode, and the control electrode 134. The net flow of negatively charged materials is from the cathode to the anode (second electrode 132). If the control electrode 134 is made neutral, or even slightly negative, negatively charged materials, such as DNA, would flow in a direction from the cathode to the anode. Once a desired fraction of the DNA passes through or by the control electrode 134, the control electrode 134 may be made more negative, thereby aiding the motion of the DNA towards the second electrode 132 and repelling undesired material which remains between the control electrode 134 and the first electrode 130 (cathode).

Figure 7:
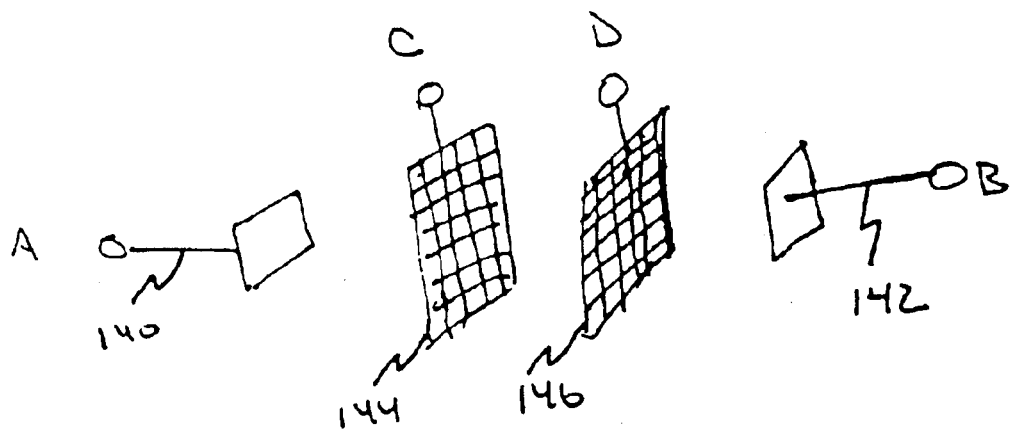
FIG. 7 is a perspective view of a multiple electrode system further including bunching electrodes.

FIG. 7 shows a perspective view of electrodes advantageously used in a buncher structure. A first electrode 140 and a second electrode 142 are arranged as cathode and anode, respectively (though the terminology may be reversed). A first control electrode 144 and a second control electrode 146 are disposed between the cathode and anode. Bunching of charged macromolecules between the first control electrode 144 and the second control electrode 146 may be achieved by applying a potential to the first control electrode 144 so as to accelerate the speed of transit of charged materials relatively closer to the first control electrode 144 than to the second control electrode 146. The second control electrode 146 is biased so as to retard the speed of charged materials which are relatively closer to the second control electrode 146 than to the first control electrode 144. Since the rate of diffusion of charged macromolecules in a solution phase environment is significant compared to the transit time through the chamber (e.g., the region defined between the first electrode 140 and second electrode 142), the bunching process serves to localize the desired charged materials within a smaller region, counteracting the effects of diffusion. In one mode of operation, once the desired amount of DNA passes the first control electrode 144, that control electrode may be placed at a negative potential which serves to further cause the negatively charged materials towards the second electrode 142 (anode). While FIG. 7 shows a 4-electrode arrangement, a buncher may be formed from the structure of FIG. 6, by operation of the electrodes in a manner described above.

Broadly stated, this aspect of the invention involves a method for selective isolation of desired charged biological materials from undesired charged biological materials in a electrophoretic system having a solution phase region, the method including at least the step of applying a repulsive potential to a first electrode so as to accelerate motion of the desired charged materials which are relatively closer to the first electrode than to the second electrode, and applying a repulsive potential to a second electrode so as to decelerate motion of the desired charged materials which are relatively closer to the second electrode than to the first electrode. Such operation results in a spatial distribution of the desired charged materials between ti the first and second electrodes is reduced.

Figure 8:
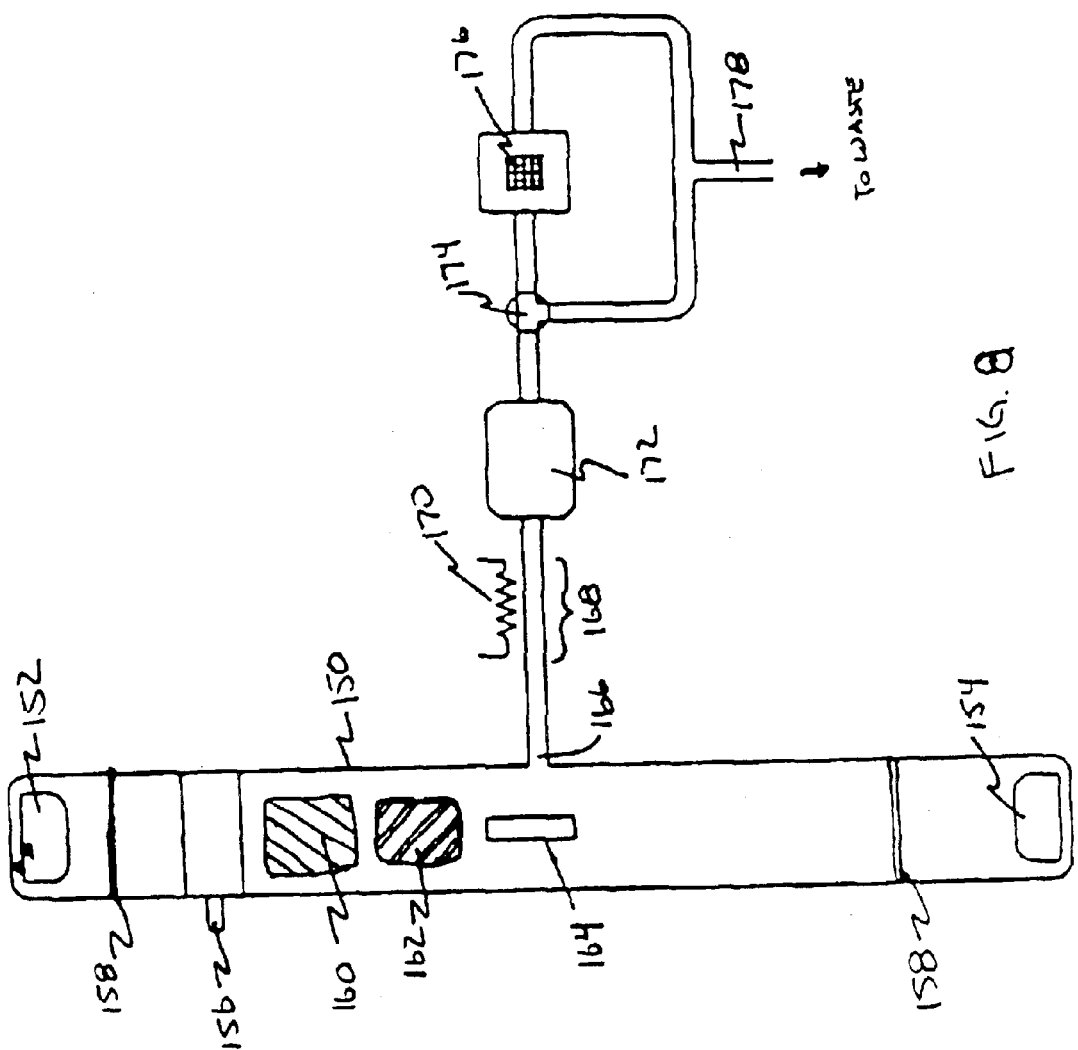
FIG. 8 is a plan view of one implementation of an integrated sample preparation an diagnostic device.
Figure 9:
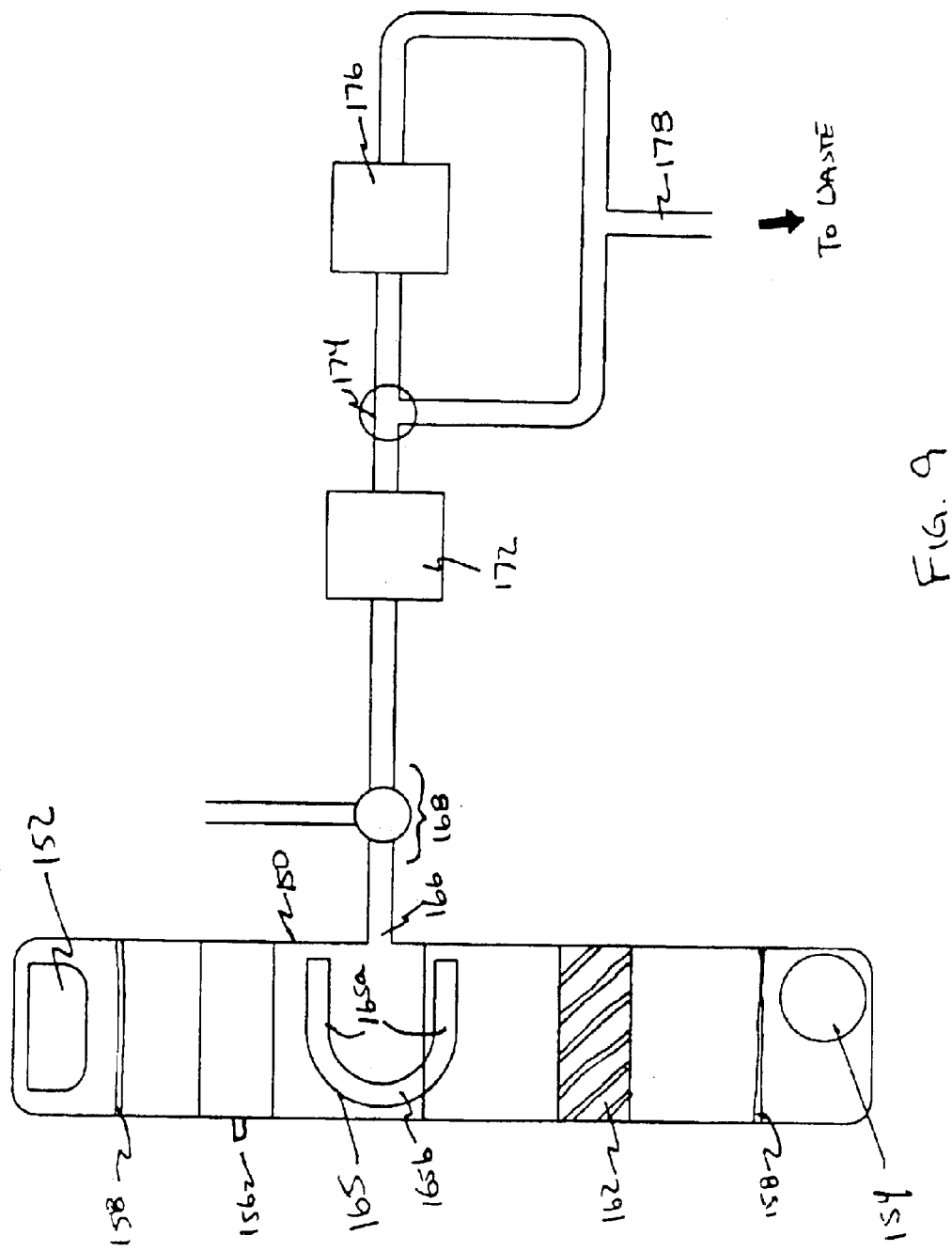
FIG. 9 is a plan view of another integrated sample preparation and diagnostic device.

FIGS. 8 and 9 show two implementations in plan view of an integrated sample preparation system of this invention. For convenience, commonly identified structures in FIGS. 8 and 9 will be labeled with the same reference numerals. FIG. 8 shows a system in which the tap 166 is disposed downstream from a protein trap region 162. FIG. 9 shows a system in which the protein trap region 162 is downstream of the tap 166.

A purification chamber 150 has disposed at the end thereof a first electrode 152 and a second electrode 154. A sample addition port 156 may comprise an input region of the purification chamber 150. Preferably, the sample addition port 156 comprises a liquid interconnect or cover seal (e.g., luer lock, face seal, slide seal). Optionally, the sample addition port 156 includes a filter, such as a 0.2 micron filter. The filter optionally serves the function of debris removal and may also provide some shearing of DNA which will reduce the viscosity of the DNA. Optionally, membranes 158 may be utilized at one or both ends of the purification chamber 150, the principal function of the membranes 158 being to isolate the sample material from the electrodes 152, 154. Optionally, a cell lysing device 160 (shown in FIG. 8) is formed in the purification chamber 150 downstream of the ample addition port 156. A protein trap 162 is disposed within the purification chamber 150. In one embodiment, as shown in FIG. 8, a protein trap 162 is disposed between the sample addition port 156 (and the cell lysing device 160 if optionally included) and the tap 166. This option is selected principally if the desired materials for diagnosis have higher electrophoretic mobility than the protein materials to be trapped. An alternative mode of operation involves the step of causing the proteins or other undesired materials to have higher degree of mobility than the desired materials, e.g., DNA. In this mode of operation, a device such as shown in FIG. 9 may be used and the undesired materials are moved through the purification chamber 150 past the tap 166 prior to arrival at the tap 166 of the desired material, e.g., DNA. Optionally, a protein trap 162 may be then included between the tap 166 and the second electrode 154.

An electrode 164 is preferably disposed within the purification chamber 150 at a point adjacent the tap 166 which intersects the purification chamber 150. FIG. 9 shows a "C-shaped" electrode 165 generally disposed adjacent to and symmetrical with respect to the tap 166. When the DNA band is passing through the region defined by the "C" and the bias of the C-electrode is then changed to negative (−), the C-shaped electrode serves to concentrate the DNA or other charged materials contained within the space defined by the "C" and to provide a focusing of the charged materials within that region, while further repelling undesired molecules outside the C-region. Additionally, when a positive (+) potential is switched to a electrode located in line with the open portion of the "C", the entire band of DNA with the "C" is focused and propelled in the new direction toward the positive electrode location. The C-shaped electrode may be considered as various subparts, which may be formed as a continuous C-shaped structure or as discreet components. First and second electrode portions 165a are disposed generally perpendicular to the line connecting the first electrode 152 and the second electrode 154. These perpendicular electrodes 165a generally serve to provide a bunching function. The side electrode portion 165b generally provides a sideways or transverse force causing the charged materials contained within the C-shaped region towards the tap 166.

The tap 166 comprises a channel or chamber leading from the purification chamber 150 to the denaturation region 168. Optionally, the denaturation may be performed by heating, such as through a resistive heater 170, or by other modes or methods known to those skilled in the art, including, but not limited to: other forms of energy input sufficient to break the DNA strands or other chemical methods known in the art. In the preferred embodiment, the width of the tap 166 is greater than 100 microns, and most preferably on the order of 1 mm. Generally, it is desired to have a medium to low surface-to-volume ratio, the preferred embodiment reducing the amount of surface area for non-specific binding of sample or other materials to the walls of the device. The tap 166 leads to the complexity reduction chamber 172. One example of a complexity reduction chamber is described below in connection with FIGS. 10–12. Optionally, a valve 174 is disposed between the complexity reduction chamber 172 and the diagnostic assay 176. In the preferred embodiment, the diagnostic assay 176 comprises an active programmable matrix electronic device. Optionally, a disposal path 178 is connected to a waste chamber.

Figure 10:
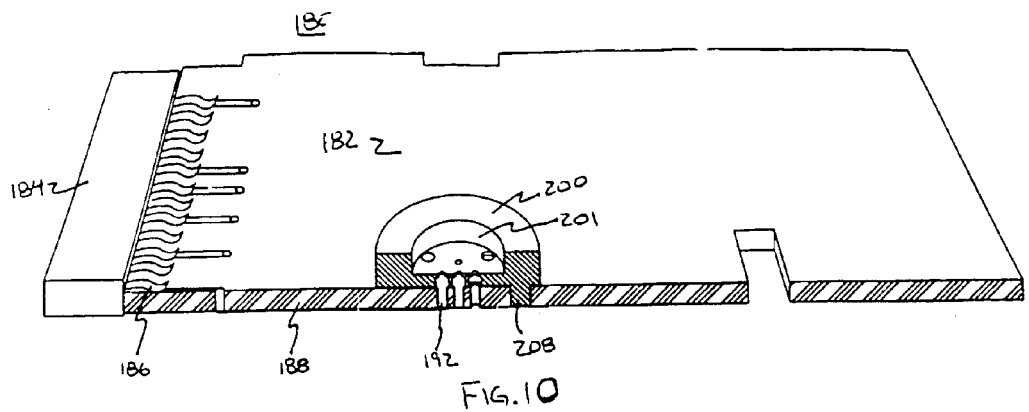
FIG. 10 is a perspective, cross-sectional view of the complexity reduction device.
Figure 11:
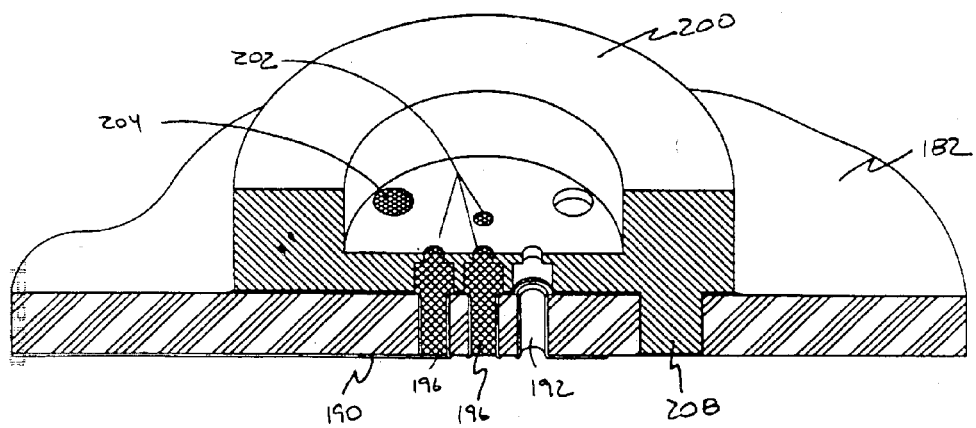
FIG. 11 is a perspective, cross-sectional close-up view of the complexity reduction device.
Figure 12:
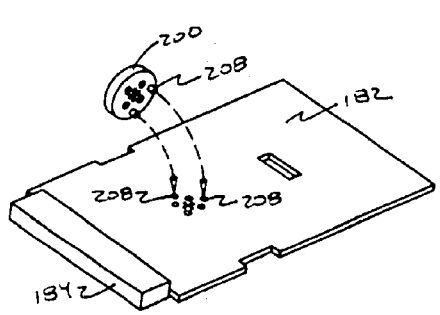
FIG. 12 is a perspective view of the complexity reduction device with the printed circuit board and complexity reduction chamber exploded from each other.

FIGS. 10, 11 and 12 show one embodiment of a complexity reduction device. The device 180 comprises a printed circuit board 182 and a chamber 200 mounted thereon. The printed circuit board 182 preferably includes an edge connector 184 to permit the interfacing of the complexity reduction system 180 to control electronics. The edge connector 184 includes a plurality of conductive fingers 186 which contact corresponding conductive portions in a mating edge connector (not shown). The printed circuit board 182 in conventional manner may include a substrate 188. The printed circuit board 182 includes conductors 190 which are patterned into conductive strips and disposed on the substrate 188. Via holes 192 are optionally formed in the printed circuit board 182, and preferably, the conduction portions 194 extend into the via holes 192. A conductive gel, such as a polymer gel, most preferably agarose, acrylamide or other conductive polymer, is placed within the via holes 192. Optionally, these materials may be cured in situ, the curing optionally enhanced or promoted by application of a potential to the conductor 194. In the preferred embodiment, a chamber 200 is attached to the printed circuit board 182. A seal 198 serves to form a hermetic seal between the chamber 200 and the substrate 188. Within the chamber 200, a sample volume 201 is formed to contain a sample for complexity reduction. Optionally, an input port and an output port may be included within the chamber 200 to provide access to the chamber volume 201. Alternatively, the sample may be supplied into the sample volume 201 through an opening at the surface. Within the chamber 200, one or more probe areas 202 form the upper portion of the via holes 192. The gel 196 preferably fills this space and terminates at the bottom of the sample volume 201. Optionally, disposal or dump areas 204 may be included within the chamber 200. Preferably, an index detent 206 is provided within the substrate 188. A matching key 208 is preferably formed on the underside of the chamber 200 to aid in indexing of the chamber 200 relative to the printed circuit board 182. As shown in FIG. 12, the chamber 200 may then be matingly engaged with the printed circuit board 182, with the keys 208 joining with the index detents 206. In operation, the polymer gel 196 includes capture probes. These capture probes then interact with the target materials in the sample and hybridize thereto. Conductive polymer may be used to fill the vias of the complexity reduction device in order to provide a matrix for DNA probe attachment, and DNA target hybridization and separation. The polymer can be mixed with protein bound DNA capture probe prior to filing the vias of the device in order to introduce polymer functionality or covalently bound capture probe may be pre-mixed with the conductive polymer. Alternatively, the probe may be electrophoretically transported into the polymer and linked by enzymatic or covalent means in order to provide additional means for attachment to the polymeric support.

In operation, the target DNA may be placed directly in the sample well of the complexity reduction device or fluidically or electrophoretically introduced into the sample chamber. The sample can be introduced in one of several different buffers, including 50 mM sodium borate pH 8, or 0.5×TBE. These buffers provide for free field electrophoretic transport of DNA at relatively low ionic strengths. Test results are shown in FIG. 17. Also, enhanced hybridization is shown for 0.5×TBE and histidine in FIG. 16. During transport, the electrodes are biased with a positive current and the target DNA is transported electrophoretically into the polymer filled vias of the device allowing the complementary target DNA to hybridize to the specific capture probe. Next, during the electronic wash procedure, the DNA which is not a specific match to the capture DNA is removed from the vias using a mild negative current. A fluidic wash removes any irrelevant DNA from the sample well and fresh buffer is then introduced. The hybridized target DNA then may be dehybridized electrophoretically using a strong negative current.

In order to maximize DNA purification, electrophoretic transport, hybridization, electronic wash and dehybridization can be performed using a variety of electronic settings. For transport and accumulation, the settings include a positive DC current of between 5 to 2,500 $\mu A/mm^2$ per polymer filled via for 10 s to 180 s (preferably: 200 to 500 $\mu A/mm^2$ for 15 to 60 s), a pulsed current of between 5 to 2,500 $\mu A/mm^2$ at a 25 to a 75% duty cycle for 15 to 180 s (preferably: 200 to 1,000 $\mu A/mm^2$, 50% duty, 15 Hz for 20 to 180 s), and a reverse linear stair starting at between 100 to 500 $\mu A/mm^2$ and ending at 0 to 150 $\mu A/mm^2$ in 15 to 90 s (preferably: starting at 250 $\mu A/mm^2$ and ending at 25 $\mu A/mm^2$ in 90 s). An electronic wash is conducted with a negative DC bias between 200 to 300 $\mu A/mm^2$ or a pulsed current of between 200 and 500 $\mu A/mm^2$ for 15 to 180 s. Dehybridization is performed at a negative DC current of 400 to 750 $\mu A/mm^2$ for 60 to 420 s.

Figure 16:
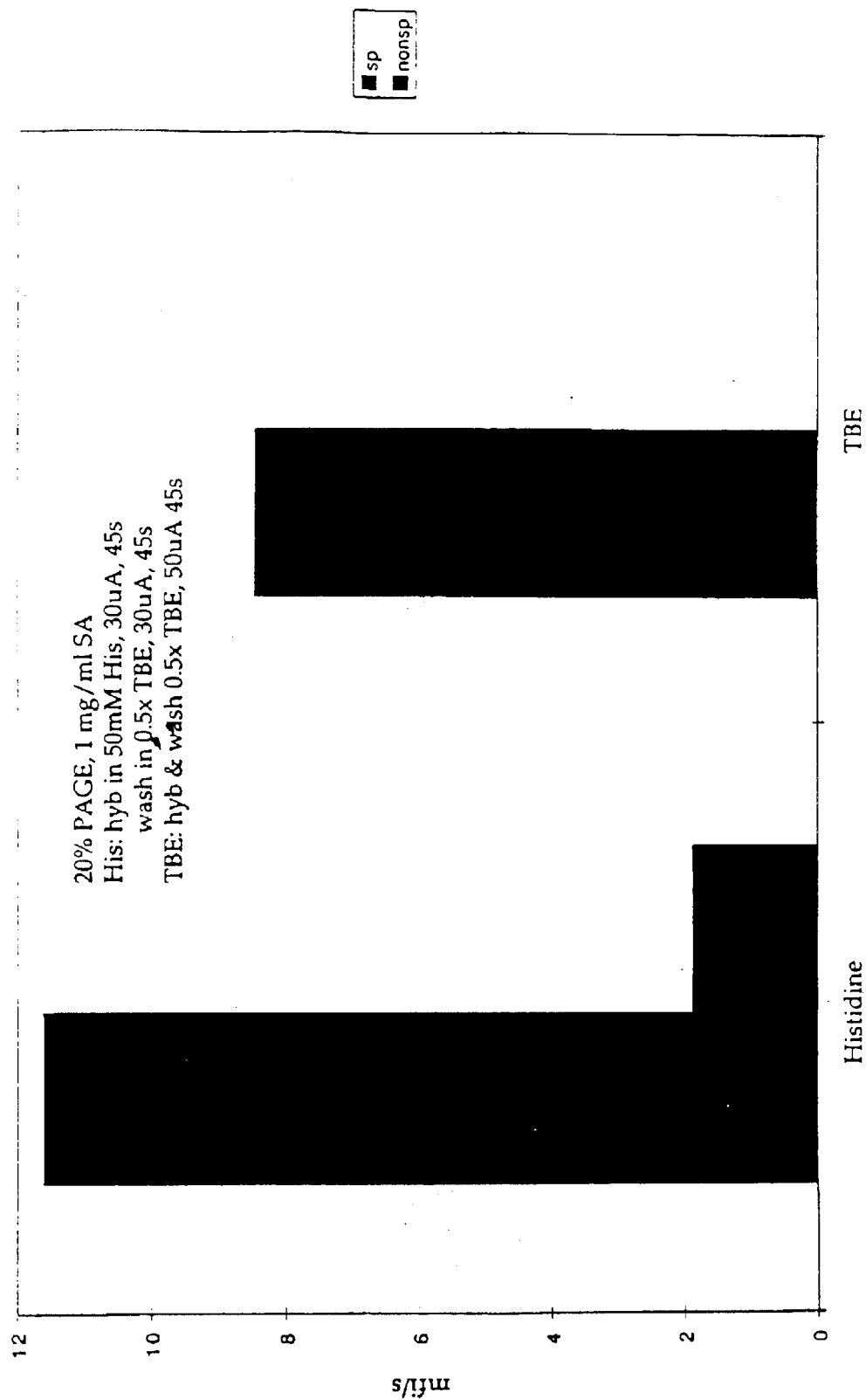
FIG. 16 is a graph comparing the operation of the complexity reduction device in different buffer solutions.
Figure 17:
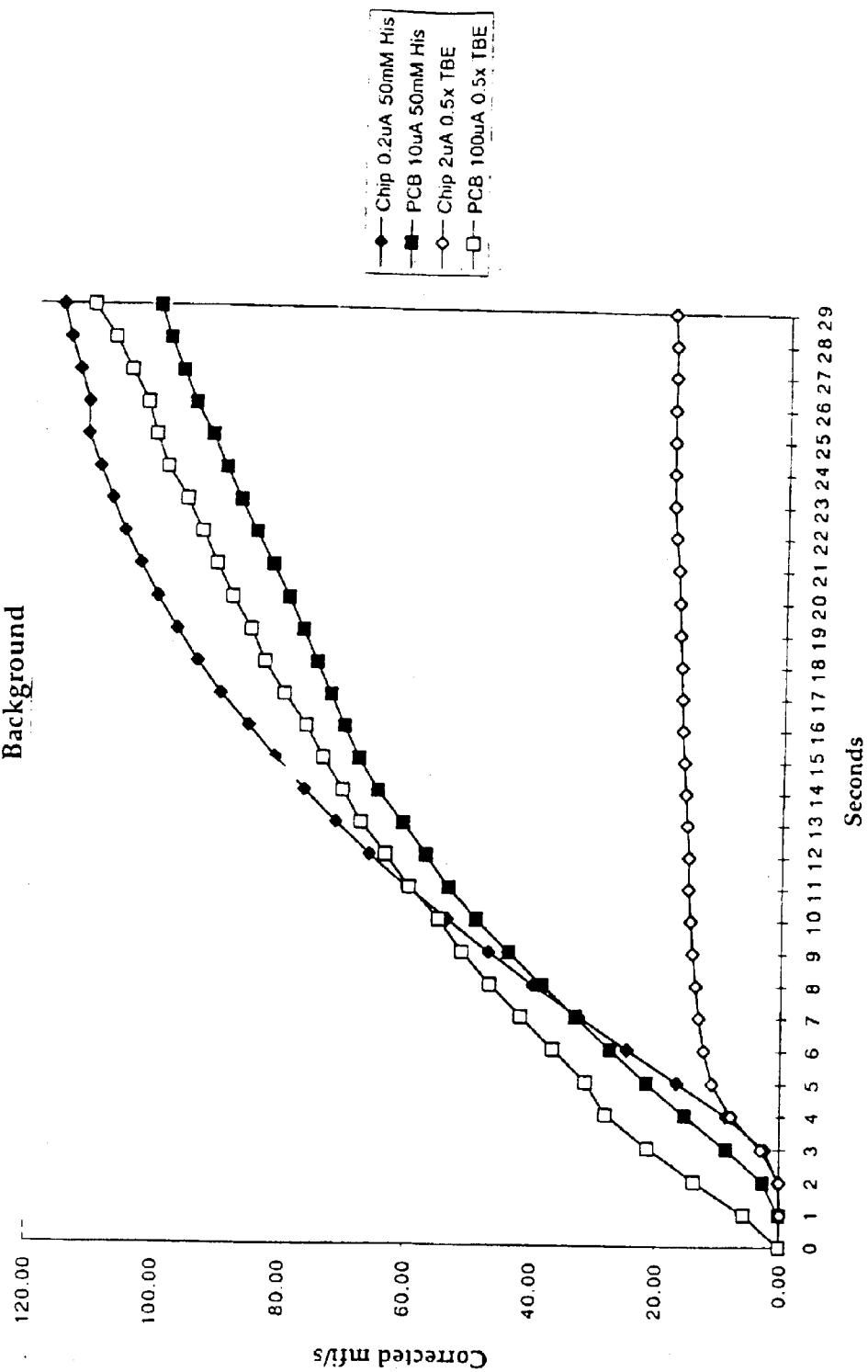
FIG. 17 is a graph of the signal accumulation for a microelectronic device in comparison to a printed circuit board based device for various buffers.
Figure 19:
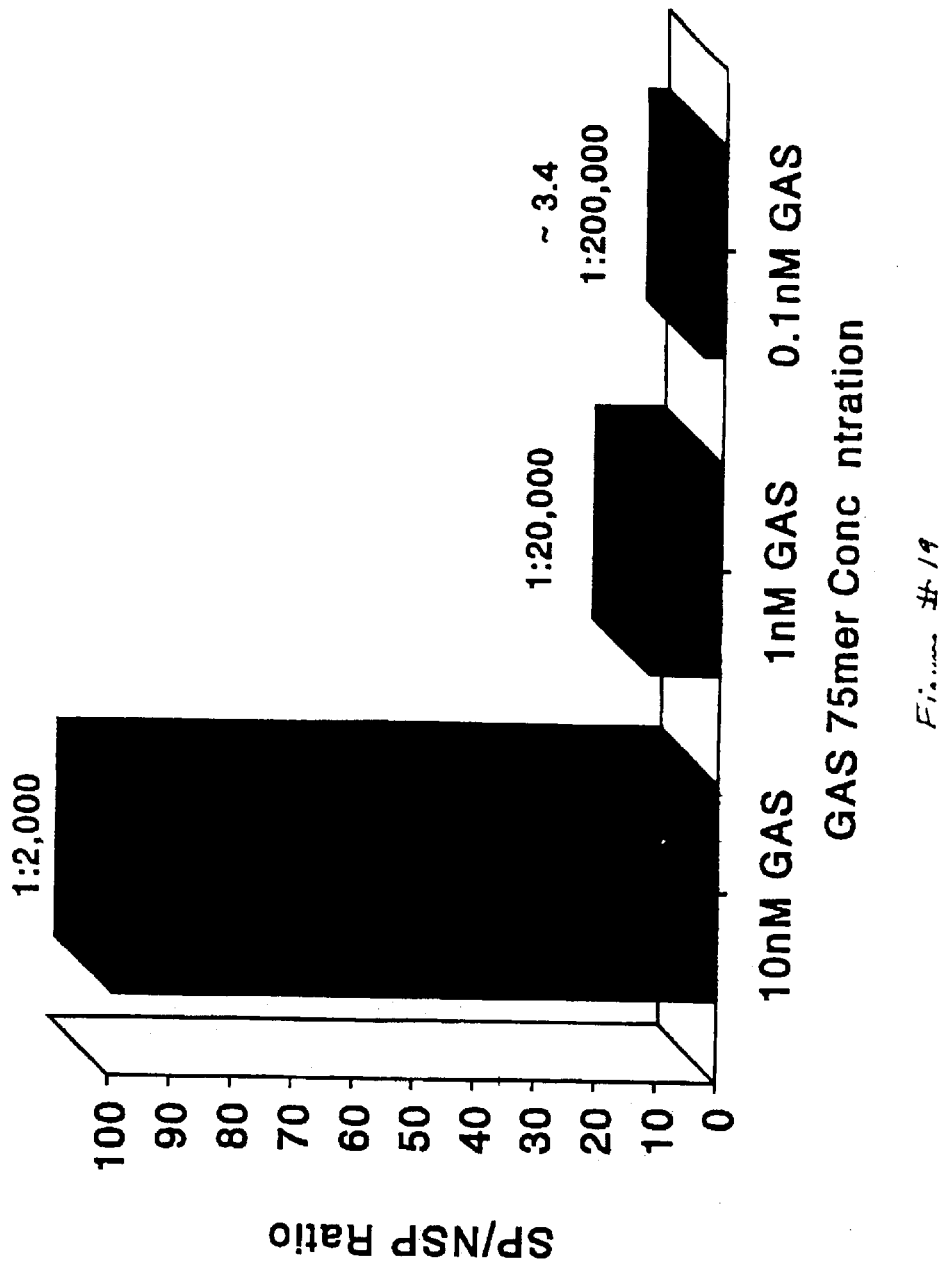
FIG. 19 is a graph of hybridization of labeled Streptococcal target DNA in the presence of an equimolar concentration of nonlabeled complementary DNA and irrelevant human DNA.

For purposes of fluorometric detection, target DNA can be labeled with a fluorophore, "reverse dot blot" hybridization, FIGS. 16 and 19. In addition, the target DNA can be detected after hybridization to the capture probe by the introduction of a fluorophore labeled strand of DNA complementary to a nonhybridized region of the target DNA "sandwich" hybridization. Alternatively, the fluorophore label can be incorporated into the target DNA which has been amplified by PCR.

Figure 13:
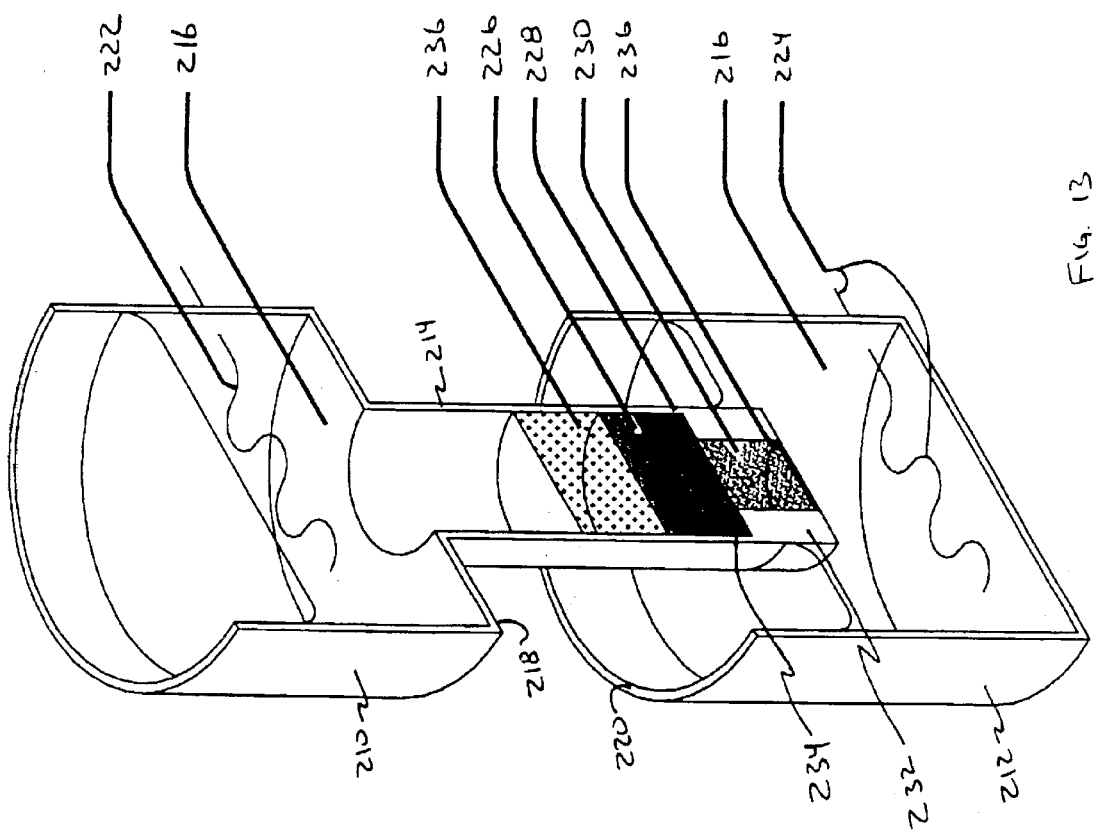
FIG. 13 is a cutaway perspective drawing of a vertically disposed sample fit preparation device.

FIG. 13 shows a perspective, cutaway view of a vertically disposed DNA or nucleic acid purification device of this invention. An upper reservoir 210 communicates with a lower reservoir 212 via tube 214 permitting fluid communication from the upper reservoir 210 to the lower reservoir 212. The reservoirs 210, 212 are adapted to receive a buffer solution 216. Optionally, the upper reservoir 210 and lower reservoir 212 may be formed so as to permit formation of a closed system, such as by causing the bottom 218 of the upper reservoir 210 to sealingly contact the top 220 of the lower reservoir 212. Alternatively, the system may be an open system. The upper reservoir 210 contains a first electrode 222 and the lower reservoir contains a second electrode 224. The first electrode 222 and the second electrode 224 may be referred to as the cathode and anode, respectively, though those terms may be interchanged given the polarity in of operation. The tube 214 preferably has an inner diameter which is smaller than the inner diameter of the reservoirs 210, 212. The tube 214 contains a polymer 226. The polymer 226 is a molecular sieve which comprises a differential mobility region. Materials which provide differential mobility for charged biological macromolecules include materials such as agarose and polyacrylamide.

In the preferred embodiment, the differential mobility material is a cast 1.5% agarose gel in 50 mM histidine, formed on a supporting membrane 228 in tube 214. Optionally, the polymer 226 is disposed adjacent a membrane 228. Preferably, the membrane 228 is porous, e.g., 5 micron pore size, and serves in part to provide a support for the formation of the polymer 226. A chamber 230 is disposed adjacent the polymer 226. Preferably, the chamber 230 has a volume which is less than that of the polymer 226, e.g., preferably being approximately 50% or less in volume, and most particularly approximately ⅓ or less in volume than the polymer 226. If the chamber 230 has a reduced volume relative to the polymer 226, a reduced inner diameter region 232 may be formed in the tube 214. This reduced inner diameter region 232 advantageously forms a ledge 234 providing an annular region on which the membrane 228 may disposed. Optionally, a second membrane 236 may define a portion of the boundary of chamber 230. The second membrane 236 preferably constitutes a molecular weight cut-off membrane, such as an ultrafiltration membrane, which serves to retain the DNA within the chamber 230, but passes smaller materials, such as proteins subjected to proteinase K. Such ultrafiltration membranes include those formed from cellulose acetate or cellulose, In the preferred embodiment, the electrodes are disposed generally parallel to the membrane (236), and at a distance from the membrane that is equal to, or greater than, the height of the collection chamber (230).

In operation, a sample is previously lysed such as by motion of glass beads acting on cells of the sample. Additionally, the sample is preferably subject to shearing, such as by movement through a relatively narrow aperture, such as an aperture of diameter of 250 microns. The sample is preferably subject to a treatment step which reduces the size of the proteins or other undesired materials so as to increase their differential mobility relative to the desired material, e.g., DNA. For example, addition of proteinase K may reduce the size of proteins, such as to 20,000 daltons or less. This application of proteinase K may be done at room temperature, though performing it at an elevated temperature, e.g., 37° C. to 50° C., increases the rate of reaction. In the preferred embodiment, the lysate cells are digested with 250 $\mu g/ml$ proteinase K, 0.5×TBE 50 mM EDTA buffer (37–50° C.) with a total volume of 50 $\mu l$. Next, a densification agent, such as sucrose, e.g., preferably 5%–20%, and most preferably substantially 8–10% serves to densify the sample. Optionally, the densified material may be combined with a dye, such as bromphenol blue. The densified, pre-prepared sample is then injected or placed above the polymer 226, such as by use of a syringe. Use of the densified sample serves to locate and concentrate the sample immediately above the polymers 226. The system is then operated to cause the electrophoretic motion of charged materials. The system is activated for a time to permit the DNA to migrate into the polymer 226, and to permit the reduced size proteins to substantially traverse the polymer 226 into the chamber 230 and lower reservoir 212. In the preferred embodiment, the sample is run into the gel for six to eight minutes, at a current of 2.25 mA, with a 1,000 V limit. The cathode additionally serves to permit attraction and destruction of the proteinase K and other positively charged materials. Optionally, fresh buffer 216 is provided in the lower reservoir 212, and the second membrane 236 may be added at this time (though it may be initially included within the device). In the preferred embodiment, the membrane 236 is a 25 kD molecular weight cutoff membrane. Next, the DNA is eluted from the polymer 226 into the chamber 230. In the preferred embodiment, the sample is eluted out of the polymer into the elution chamber 230 for approximately two minutes, with the 1,000 V limit. The DNA is then extracted from the chamber 230, such as by piercing or providing a port and valve arrangement.

Though the system of FIG. 13 is shown in a vertical arrangement, it may be performed in a horizontal arrangement. The vertical arrangement permits a constant contact area between the sample solution 236 and the polymer 226. Further, the use of the densification agent permits the localization of the sample solution 236 immediately adjacent the polymers 226, reducing the time necessary for the sample solution 236 to reach the polymer 226. In a horizontal arrangement, as shown in FIG. 13, a polymer (or gel or membrane) dam can be used to maintain the separation of the sample from the electrode buffer to prevent mixing.

Figure 14:
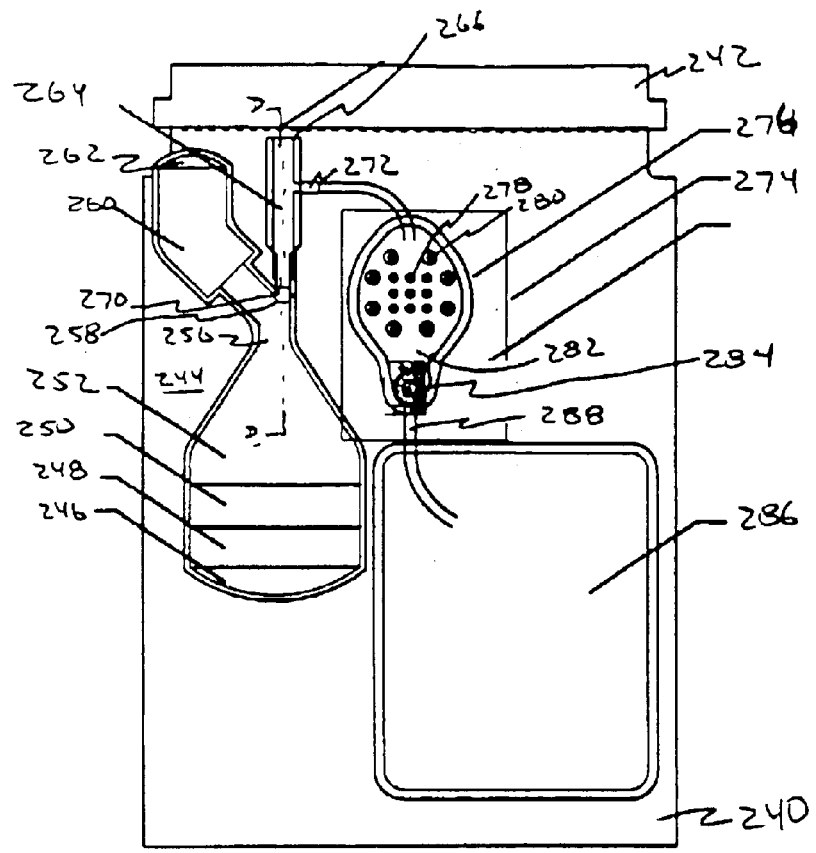
FIG. 14 shows a plan view of a horizontal integrated sample preparation, complexity reduction, diagnostic and disposal device.
Figure 14:
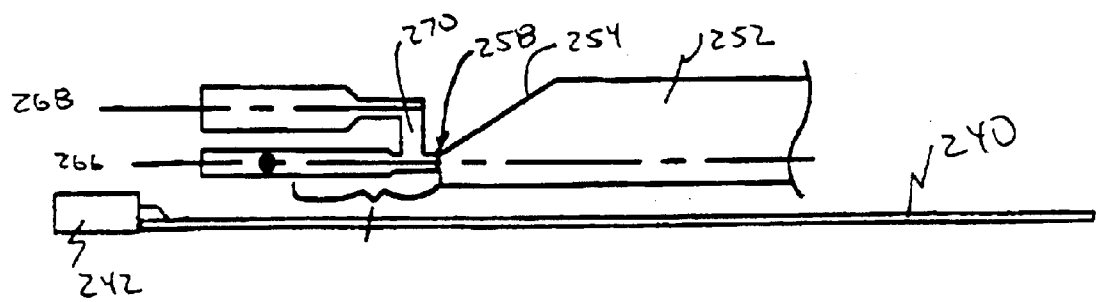

FIG. 14 shows a plan view of an integrated device including a sample preparation, complexity reduction, diagnostic region and disposal region. FIG. 14A shows a cross-sectional view of FIG. 14 along the line A–A'. A support member 240, such as a printed circuit board, preferably serves to support the various components described below. Optionally, an edge connector 242 may provide electrical connection to control electronics, as discussed previously in connection in FIGS. 10–12. A sample preparation region 244 preferably includes a first buffer containing region 246 which also is in electrical communication with an electrode. A material 248 such as a gel or other conductive material is disposed between the buffer region 246 and the input port 250. In the preferred embodiment, the input port 250 includes a cover, which may be optionally removed for sample input or which can be sealed and pierced once the sample is placed within the sample port 250. A DNA trap 252 is disposed between the input port 250 and the protein trap 260. Preferably, the DNA trap 252 narrows or constricts as materials are electrophoresed through the DNA trap 252. In one embodiment, a sloped upper portion 254 and inwardly sloped side walls 256 serve to form a constriction at the gel boundary 258. Such a structure provides a concentrating effect. Preferably, the protein trap 260 and the buffer space 264 are formed in a y-shaped manner. The protein trap 260 then contacts the buffer space 262 which includes an electrode.

The sample preparation structure 244 operates generally as follows. First, a sample is placed in the input port 250. Electrophoretic action of the electrodes causes conduction of the charged macromolecules from a direction connecting the buffer region 246 towards the buffer region 262. In the preferred embodiment, the sample is subject to a preprepation step which lyses the cells and digests the protein, resulting in proteinaceous material which has a relatively higher mobility than the DNA through the DNA trap 252. Thus, as electrophoresis continues, the protein materials arrive at the protein trap 260 prior to the arrival of the DNA. After the proteins arrive at the protein trap 260, the electrode and buffer region 262 is turned neutral and the electrode and buffer region 264 is biased from neutral to positive. The DNA moving through the DNA trap 250 are then attracted by a positive potential applied to the buffer space 264. In this manner, the proteins are shunted to the protein trap 260 whereas the DNA, most likely at a later time, are shunted to the chamber port 266. The DNA concentration volume is shown in FIG. 14A as that portion beyond the gel boundary 258 within the buffer space 264.

In one aspect of the invention, the buffer space 264 includes as an input a chamber port 266 coupled to one end of the buffer space 264 and a second port or inlet port 268 which is fluidically coupled to the opposite end of the buffer space 264, as shown in FIGS. 14 and 14A being connected by a bound tube 270 to the buffer space 264. In operation, the inlet port 268 and chamber port 266 may receive the same or different liquid or gas, such as a buffer, a reagent or an air slug. By operation of the materials provided to the inlet port 268 and chamber port 266, a hydraulic or pneumatic ram may result. For example, if the buffer space 264 contains DNA which has been eluted from the DNA trap 252 into the buffer space 264, that material may be forced into the connector 272 by forcing fluid, e.g., buffer, into the inlet port 268 causing the DNA to move into the connector 272. Advantageously, air slugs may be used to separate various fluidic materials. Additionally, fluid may be withdrawn from the inlet port 266, 268 to cause the movement of other materials in a direction generally opposite to the normal processing flow direction.

The structure shown in FIGS. 14 and 14A additionally includes the connector 272 being in communication with the complexity reduction region 274. An exterior containment vessel 276 defines the outer edge of the complexity reduction region 274. One or more probe areas 278, having the structure and function described previously with respect to FIGS. 10–12, may be utilized. Similarly, one or more dump areas 280 may be disposed within the complexity reduction region 274 as described in connection with FIGS. 10–12. Preferably, a volume reduction region 282 connects the complexity reduction region 274 to the diagnostic region 284. The reduced volume region 282 serves a concentrating function. The structure and function of the diagnostic portion 284 may include any known diagnostic, but preferably includes an electronically enhanced hybridization/dehybridization device such as described in "Active Programmable Electronic Devices for Molecular Biological Analysis and Diagnostics", U.S. Ser. No. 08/146,504, filed Nov. 1, 1993, incorporated herein by reference. Preferably, a connector 288 provides fluid communication to a waste region 286. The waste region 286 preferably is a fully contained volume so as to avoid biological contamination.

While the methods and devices herein have generally been described as a serial system, e.g., a sample preparation section, a complexity reduction section and an assay section, some or all of the stages may be performed in a parallel or multiplexed format. In one embodiment, two or more parallel sets, each comprising a sample preparation region, a complexity reduction region and an assay may be used. As an alternative embodiment, two or more sets of sample preparation sections may provide output to a smaller number, e.g., one, complexity reduction region, preferably followed by an assay. Alternatively, two or more sets of a sample preparation section and a complexity reduction region may provide their outputs to a smaller number, e.g., one, assay. Other variations and combinations consistent with the invention will be apparent to those skilled in the art.

Further, while the description in the patent refers often to DNA, it will be understood that the techniques may be applied to RNA or other charged macromolecules, when consistent with the goals and functions of this invention. When the inventive methods and apparatus are used for RNA at the time of lysis, the user would preferably add RNAse inhibitors and RNAse free DNAse to remove DNA. The remainder of the purification process would follow as before. The isolation of poly A RNA, which includes most of the mRNA, and removal of ribosomal RNA is preferably performed in the complexity reduction chamber. Oligo dT probes could optionally be used to bind the polyA RNA during electronic hybridization and unhybridized RNA, mostly ribosomal RNA, would be removed. To release the poly A RNA, electronic dehybridization could preferably be employed. Similarly, a specific sequence of mRNA could be isolated by using probes complementary to that sequence in the complexity reduction device. Electronic hybridization would be performed as for DNA targets and the unhybridized, irrelevant RNA would be removed. The desired mRNA species would be eluted from the probes by electronic dehybridization.

The sources and control systems for supply of the potential, current and/or power to any of the electrodes of these inventions may be selected among those known to persons skilled in the art. The voltage and/or current may be supplied with either fixed current or fixed voltage, with the other variable permitted to float, optionally subject to limits or maximum values. The control system may be analog or digital, and may be formed of discrete or integrated components, optionally including microprocessor control, or a combination of any of them. Software control of the systems is advantageously utilized.

EXPERIMENTAL DATA

Example 1
Comparison of FIG. 13 Device to Qiagen

The relative performance of a device as shown in FIG. 13 was compared to the prior art Qiagen system. For the comparison, the preparation and operation of the FIG. 13 device was as follows.

First, 50 mL of a stationary phase suspension culture of Staphylococus aureus cells was pelleted and resuspended in 1000 µl of 0.5×TBE, 50 mM EDTA, and lysed by vortexing in the presence of glass beads. Then, RNA and protein were fragmented by digesting with 50 µg/ml RNAse and 250 µg/mL proteinase K for 40 minutes at 50° C. Next, the sample density was increased by the addition of 5 µl of 40% sucrose to 20 µl sample, which is roughly equivalent to $10^9$ cells, to achieve a final concentration of 8%. Prior to loading the sample, the device was filled with 50 mM histidine and then, 25 µl of sample was then loaded in the sample solution zone 236. In other experiments, volumes as high as 100 µl have been used with similar results. Next, the electrodes were connected to a power supply and current was sourced at 2.5 mA. In other experiments, currents as low as 1 mA have been used with similar results except that transport was slowed. After 3 minutes, the power was turned off, the barrel was removed, and a cellulose acetate membrane with a 25 kD molecular weight cutoff was inserted as second membrane 236. The solution was also removed and fresh 50 mM histidine was added to the device. After reassembly, the power was turned on and the sample was eluted into chamber 230 formed by the cellulose acetate membrane 228 which supports the gel and the 25 kD cutoff cellulose acetate membrane 236. To remove the eluted sample, the power is turned off, the barrel was removed, a pipette/syringe is used to puncture the 25 kD cutoff membrane and the sample solution was withdrawn. The total time for all of the electrophoretic steps was less than 5 minutes. The sample was analyzed by agarose gel electrophoresis and spectrophotometry. Gel electrophoresis showed that the DNA was approximately 20 kbp in length and that the yield was approximately 20%.

For comparison, a crude sample prepared by the same method of lysis and digestion was processed in the Qiagen device. The Qiagen device was operated in accordance with its instructions. A comparison to results obtained with the Qiagen device is as follows.

Figure 15:
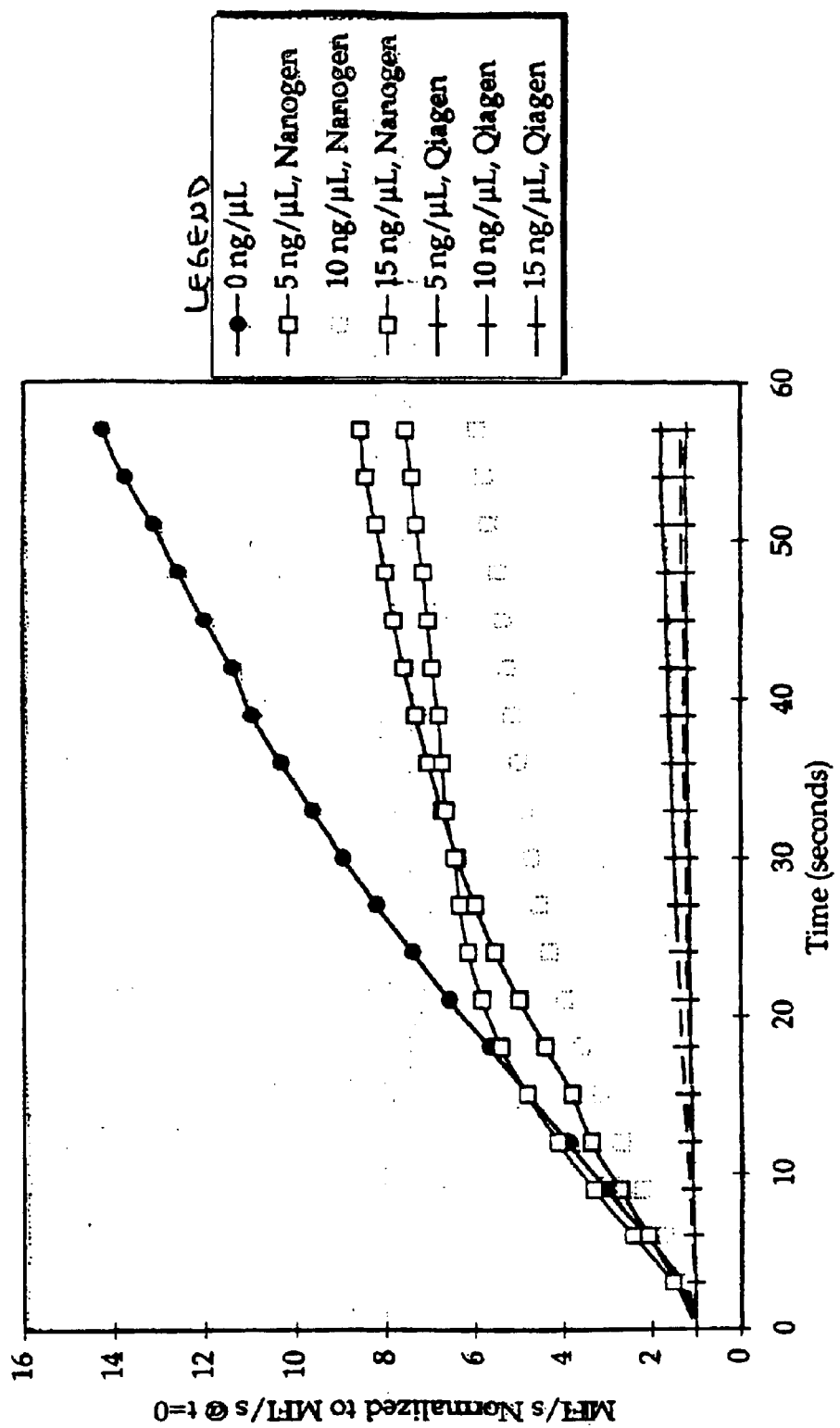
FIG. 15 is a graph of target DNA transport in the presence of S. aureus Genomic DNA purified by the device of FIG. 13 compared to the prior art Qiagen method, as a function of time.

Optical density readings were performed and the ratio of the optical density at 260 nanometers to 280 nanometers was determined. The device of FIG. 13 provided a ratio of from 1.6 to 1.8 on various operations, in contrast, the Qiagen device providing a result of less than 1.3 with the same material (the Qiagen literature does state that a ratio of 1.7 to 1.9 can be obtained). Thus, in the actual testing on this sample, the device of FIG. 13 provided purified DNA. Secondly, the transport of the prepared sample on a microelectronic chip constructed as disclosed in "Active Programmable Electronic Devices for Molecular Biological Analysis and Diagnostics", Ser. No. 08/146,504, filed Nov. 1, 1993, was better than the transport on the same device of the Qiagen prepared material. It is believed that the Qiagen material has a relatively high residual salt content, and that therefore the transport on the chip was poorer than in the case of transport of material prepared by the method and structure of FIG. 13. FIG. 15 shows test results for transport of samples prepared by the device of this invention as compared to sample prepared by the Qiagen device. Third, sample preparation was significantly faster with the FIG. 13 device, approximately 5 minutes (6.5 minutes in one test) in comparison to over two hours for the Qiagen device. Finally, the yields for both methods were similar, approximately 20%.

Example 2
Performance of FIG. 1 Device

A device was prepared with the same structural components as FIG. 1, though its actual shape was as disclosed here. The purification device was constructed from polymethacrylate (PMA) generally as shown in FIG. 1. To allow the insertion of different materials 22, 16 and 24, the device is assembled from separate sections of PMA whose ends meet at the lines indicated by the spacer region 16. The sections are held together by screws which run longitudinally. Electrodes made of Pt wires were attached to electrodes 26, 28. The wires protruded into electrode chambers 18, 20. Electrode chambers 18, 20 were each filled with 300 µl TAE, 250 mM HEPES. An Elutrap ultrafiltration cellulose acetate membrane from Schleicher and Schuell was inserted between PMA sections at position membrane 24 and a cellulose acetate membrane with a 25 kD cutoff from Sialomed was inserted at membrane position 22 to separate the electrode chambers 18, 20 from the sample chambers 12, 14. The sample chambers 12, 14 were filled with 75 µl each of TAE, 250 mM HEPES. Although different membranes have been inserted at spacer region 16 to achieve separation of DNA from protein, in this experiment, spacer region 16 contained an Immobilon P membrane (PVDF with 0.45 µm pores) from Millipore. The membrane was wetted with methanol and soaked in 1×TAE, 250 mM, 0.1% Triton ×100 prior to loading into region 16. A crude sample, a 162 µl of a mixture of a protein, 48.5 μg of Bodipy Fluorescein labeled BSA, and 0.79 μg of a Bodipy Texas Red labeled 19 mer in 1×TAE, 250 mM HEPES was loaded into chamber 12. After the addition of the sample, first electrode 26 was biased negative and second electrode 28 was biased positive for 2.75 minutes at 10 mA. As a result, the sample was electrophoretically transported to spacer region 16. The labeled DNA passed through the membrane and was collected on the other side of the membrane in right central chamber 14. The amounts of DNA and BSA were determined by fluorimetry. The results show that the yield of DNA was 40% an that 78% of the BSA was removed.

Example 3
Performance of Complexity Reduction Device

Figure 18:
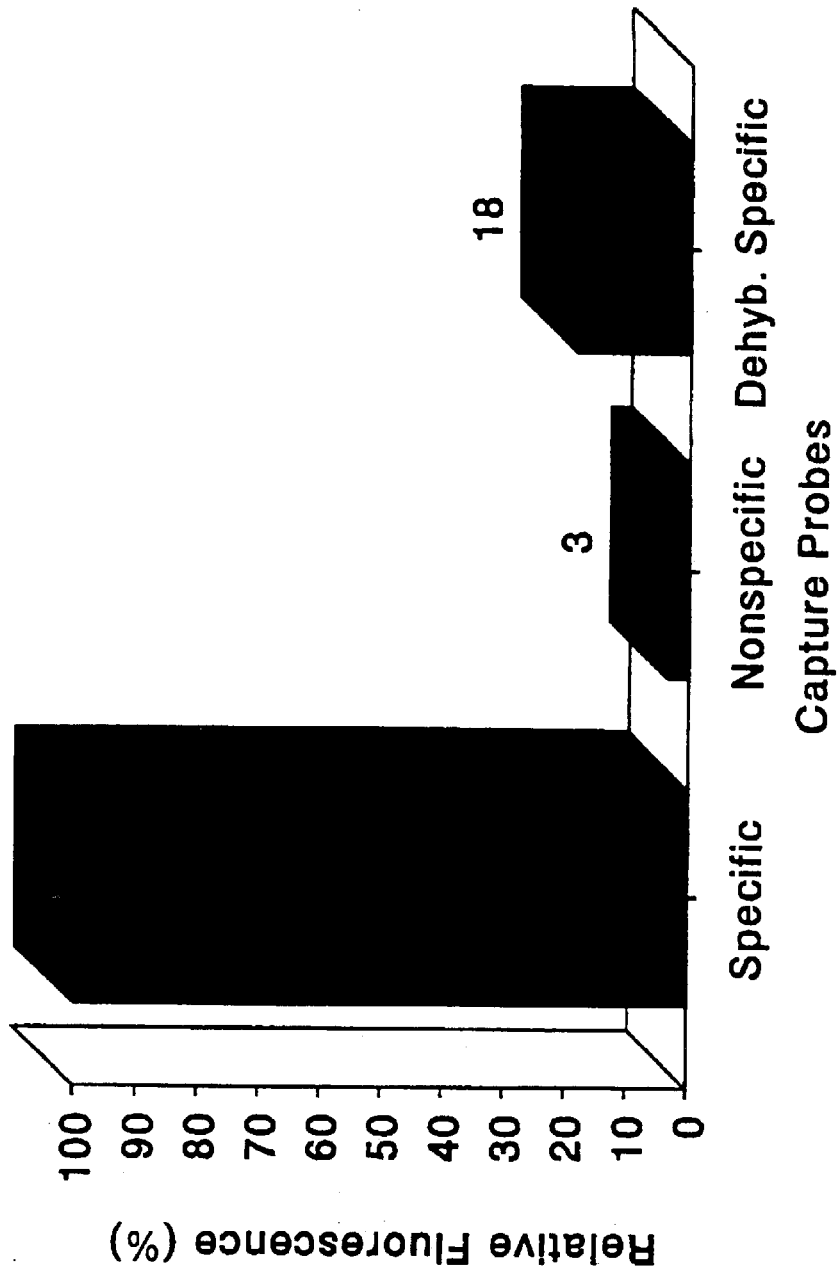
FIG. 18 is a graph of relative target signal levels determined for specific and nonspecific probes following transport and electronic wash, and after dehybridization using a Texas Red Bodipy™ labelled Streptococcal target sequence in the presence of irrelevant human DNA per 40 μL.

In Group A Streptococcal (GAS) experiments, FIGS. 18 and 19, the polymer is pre-mixed with a 20 μM concentration of a 25 mer streptavidin-biotin bound capture probe. In GAS experiments, FIGS. 18 and 19, 40 μL aliquots of target DNA are placed into the sample well in 50 mM histidine. Electrophoretic transport was conducted using a linear stair starting at 250 $\mu A/mm^2$ and ending at 25 $\mu A/mm^2$ an the electronic wash was conducted using a 250 $\mu A/mm^2$ pulse for 45 s and 120 s, respectively. Dehybridization, FIG. 18, was conducted at 400 $\mu A/mm^2$ for 150 s in 0.5×TBE. Results from FIG. 18 show a purification ratio of approximately 33-fold (100:3) and a recovery of 82% of the pure hybridized target. FIG. 19 shows purification of a specific target in increasing ratios of irrelevant DNA with a purification ratio of 3.4 fold in the presence of a 200,000 fold mass excess of irrelevant material.

Although the foregoing invention has been described in some detail by way of illustration and example for purposes of clarity and understanding, it will be readily apparent to those of ordinary skill in the art in light of the teachings of this invention that certain changes and modifications may be made thereto without departing from the spirit or scope of the appended claims.

We claim:
1. A system for the active biological sample preparation of materials comprising:

a sample addition port, a purification chamber, the purification chamber being positioned downstream of the sample addition port, and including at least a first electrophoretic solution, and first and second electrophoresis electrodes and a membrane at one end of the purification chamber, a protein trap within the first electrophoretic solution, a tap connected to the purification chamber, a denaturation chamber positioned downstream of the tap, a complexity reduction chamber positioned downstream of the denaturation chamber, and a diagnostic chamber positioned downstream of the complexity reduction chamber.

2. The system of claim 1 further including a cell lysing device disposed between the sample addition port and the purification chamber.

3. The apparatus of claim 1 further including a third electrode, the third electrode located adjacent the tap and adapted to move materials from the purification chamber to the tap.

4. The apparatus of claim 3 wherein the electrode is a C shaped electrode.

5. The apparatus of claim 3 wherein the third electrode includes:

first and second portions generally disposed in a direction which is oblique to the axis defined by the first and second electrodes, and a third portion positioned for driving material towards the tap.

6. The system of claim 1 further comprising a reagent causing cell membrane disruption disposed between the sample addition port and the purification chamber.

* * * * *